(12) United States Patent
Downes et al.

(10) Patent No.: US 9,797,875 B2
(45) Date of Patent: Oct. 24, 2017

(54) AUTOMATED FILTER CHANGER

(71) Applicant: Hanson Research Corporation, Chartsworth, CA (US)

(72) Inventors: Gary Charles Downes, Moorpark, CA (US); Steven William Shaw, Simi Valley, CA (US)

(73) Assignee: TELEDYNE INSTRUMENTS, INC., Thousand Oaks, CA (US)

( * ) Notice: Subject to any disclaimer, the term of this patent is extended or adjusted under 35 U.S.C. 154(b) by 393 days.

(21) Appl. No.: 14/537,737

(22) Filed: Nov. 10, 2014

(65) Prior Publication Data

US 2016/0131673 A1 May 12, 2016

(51) Int. Cl.
*G01N 33/15* (2006.01)
*G01N 35/00* (2006.01)
*G01N 35/04* (2006.01)

(52) U.S. Cl.
CPC ..... *G01N 33/15* (2013.01); *G01N 2035/0091* (2013.01); *G01N 2035/00198* (2013.01); *G01N 2035/00475* (2013.01); *G01N 2035/0425* (2013.01)

(58) Field of Classification Search
CPC ..... B23P 19/001; B23P 19/002; B23P 19/003; B23P 19/004; B23P 19/006; B23P 19/007; B23Q 7/003; B23Q 7/006; B23Q 7/02; B23Q 7/05; B23Q 7/055; B23Q 7/12; B23Q 2707/05; B23Q 2707/16; G01N 33/15; G01N 2035/00198; G01N 2035/00475; G01N 2035/0412; G01N 2035/0425

USPC ..... 29/771, 809; 221/93, 133, 277
See application file for complete search history.

(56) References Cited

U.S. PATENT DOCUMENTS

| 3,095,114 | A | * | 6/1963 | Tobias | G07F 5/26 |
| | | | | | 221/114 |
| 3,244,320 | A | * | 4/1966 | Vedvik | B65B 19/34 |
| | | | | | 221/124 |
| 3,392,881 | A | * | 7/1968 | Eriksen | A22C 25/08 |
| | | | | | 221/213 |
| 4,232,717 | A | * | 11/1980 | Allgaier | B65B 5/06 |
| | | | | | 141/179 |

(Continued)

OTHER PUBLICATIONS

808 Filter Changer, Agilent Technologies, Inc., Aug. 31, 2011, U.S.A., www.agilent.com/lifesciences/dissolution.

(Continued)

*Primary Examiner* — Christopher M Koehler
(74) *Attorney, Agent, or Firm* — Cislo & Thomas LLP

(57) ABSTRACT

An automatic filter changer that automatically inserts and removes a filter from a fluidic path. Filters are introduced into the automatic filter changer in stacks. The lead filter and each stack is removed from its respective stack one by one by a filter separator. The separated filters are deposited onto a shuttle plate which moves the filters into their respective fluidic paths. Fluid couplers connect to each filter to complete their respective fluidic paths and allow fluids to be filtered before sampling. Once collection of the samples is complete, the filters are removed from the fluidic path and discarded or saved for reuse. The shuttle path is returned to its original position to receive new filters to repeat the process again. A graphic user interface is provided to allow the user to program a specific set of instructions to automate the entire process.

13 Claims, 19 Drawing Sheets

(56) References Cited

U.S. PATENT DOCUMENTS

| | | | | |
|---|---|---|---|---|
| 4,298,449 | A * | 11/1981 | Ida | G01N 27/44704 |
| | | | | 204/600 |
| 5,127,278 | A * | 7/1992 | Benz | G01N 13/00 |
| | | | | 73/866 |
| 5,482,626 | A * | 1/1996 | Lohnes | G01N 1/4077 |
| | | | | 210/325 |
| 6,082,582 | A * | 7/2000 | Chiou | B23Q 7/001 |
| | | | | 221/168 |
| 6,220,450 | B1 * | 4/2001 | Weeder | B67B 1/005 |
| | | | | 209/509 |
| 6,578,259 | B2 | 6/2003 | Duckett | |
| 2003/0024107 | A1 * | 2/2003 | Duckett | B01D 29/01 |
| | | | | 29/700 |
| 2013/0248545 | A1 * | 9/2013 | Thongjitti | B65D 83/0016 |
| | | | | 221/1 |

OTHER PUBLICATIONS

FS7, Stand-Alone Filter Station, Sotax Solutions for Pharmaceutical Testing, www.sotax.com, Swizerland.
Filter Changer—FC 08, Labindia Analytical, http://labindia-analytical.com/fc08.html.
Erweka, AFC 825 Filter Changer, http://www.erweka.com.
Dissolution Automation Pumps and Filter Changer, www.pharma-test.com.

* cited by examiner

AUTOMATED FILTER CHANGER

TECHNICAL FIELD

This invention relates to an apparatus for automatically changing syringe type filters of different styles, manufactured by multiple vendors for use with devices such as a drug dissolution testing system.

BACKGROUND

A dissolution testing system may be used to determine the dissolution characteristics of a particular drug in solid, gel, capsule, caplet, gel cap, or similar forms. The dissolution testing system utilizes testing vessels containing media into which the drug is dissolved. A sample of the media containing the dissolved drug is transferred to a collection device so that the amount of drug dissolved can be measured. This can be repeated at various time intervals so that a drug's dissolution rate over time can be determined.

In some instances, prior to collection, a sample of the media containing the dissolved drug may require filtration. Current automated filtration systems are inconvenient to use, susceptible to jams, and susceptible to corrosion. For example, current filtration systems make it inconvenient if the user chooses not to use a filter for a particular sample. The fluidic path would need to be changed by disconnecting the fluid tubing and then reconnecting it in a different configuration to remove the filter changer from the fluidic path, allowing the system to then sample without filtration. This is inconvenient when dealing with a large number of samples. In addition, current filtration systems are subject to frequent jamming because of the method by which the filters are loaded in the system. Also, various components of existing filtration systems may be subject to corrosion.

For the foregoing reasons, there is a need for a filtration system that is easy to use, reliable, and durable, and can be used in conjunction with any dissolution system without many modifications.

SUMMARY

The present invention is directed to an automated filter changing apparatus for use with a dissolution testing machine, the present invention making available the option of filtering fluids from a dissolution testing machine. The automated filter changing apparatus allows filters to be automatically placed into the fluidic path, if desired. In addition, the apparatus can remove the filter from the fluidic path, discard the used filter into a bin, or hold the removed filter for another sample.

The automated filter changing apparatus utilizes a unique pair of rollers to separate filters from their respective stacks in a sequential order so that only one filter is removed at a time, which reduces the amount of power or torque required to release or remove filters from their respective stacks. Filters can be separated one at a time by utilizing angularly offset indentations on the aforementioned rollers.

A shuttle plate is used to catch a filter separated from its filter stack (referred to as a separated filter) and transport the separated filter to a fluid coupler to filter fluids from a dissolution machine, and the like. A centering plate used in conjunction with the shuttle plate aligns the separated filter properly with the fluid coupler. The shuttle plate is also configured to remove filter in the event filtration is not desired.

The system is contained in a corrosion resistant housing. The system is programmable to run a variety of protocols, and may have a wired or wireless connection to connect to the Internet to update firmware and the like. In some embodiments, the system may be able to receive a USB flash drive for firmware updates, and for storing data. In some embodiments, the system receives instruction from the dissolution machine or some other smart host.

A variety of different types of filters and filter sizes may be used with the system. In some embodiments, various components may be adjusted to accommodate different sizes of filters.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The terminology used in the description of the invention herein is for the purpose of describing particular embodiments only and is not intended to be limiting of the invention. As used in the description of the invention and the appended claims, the singular forms "a". "an" and "the" are intended to include the plural forms as well, unless the context clearly indicates otherwise. In addition, some components may be described in singular form, but can be replicated and the description of the singular form applies to the replicated forms. It will also be understood that the term "and/or" as used herein refers to and encompasses any and all possible combinations of one or more of the associated listed items.

Figure 1:
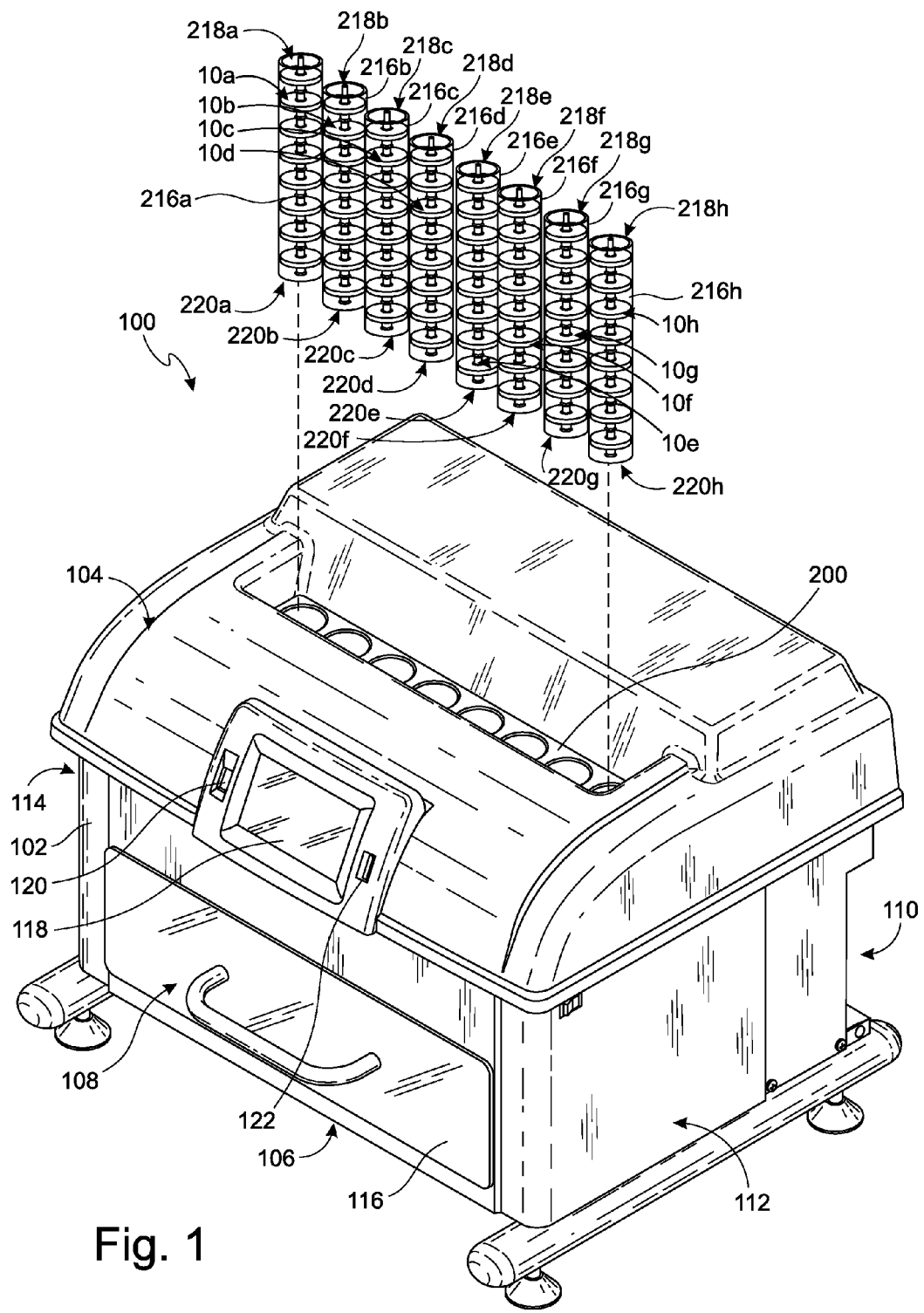
FIG. 1 shows a front, perspective view of an embodiment of the present invention.
Figure 2:
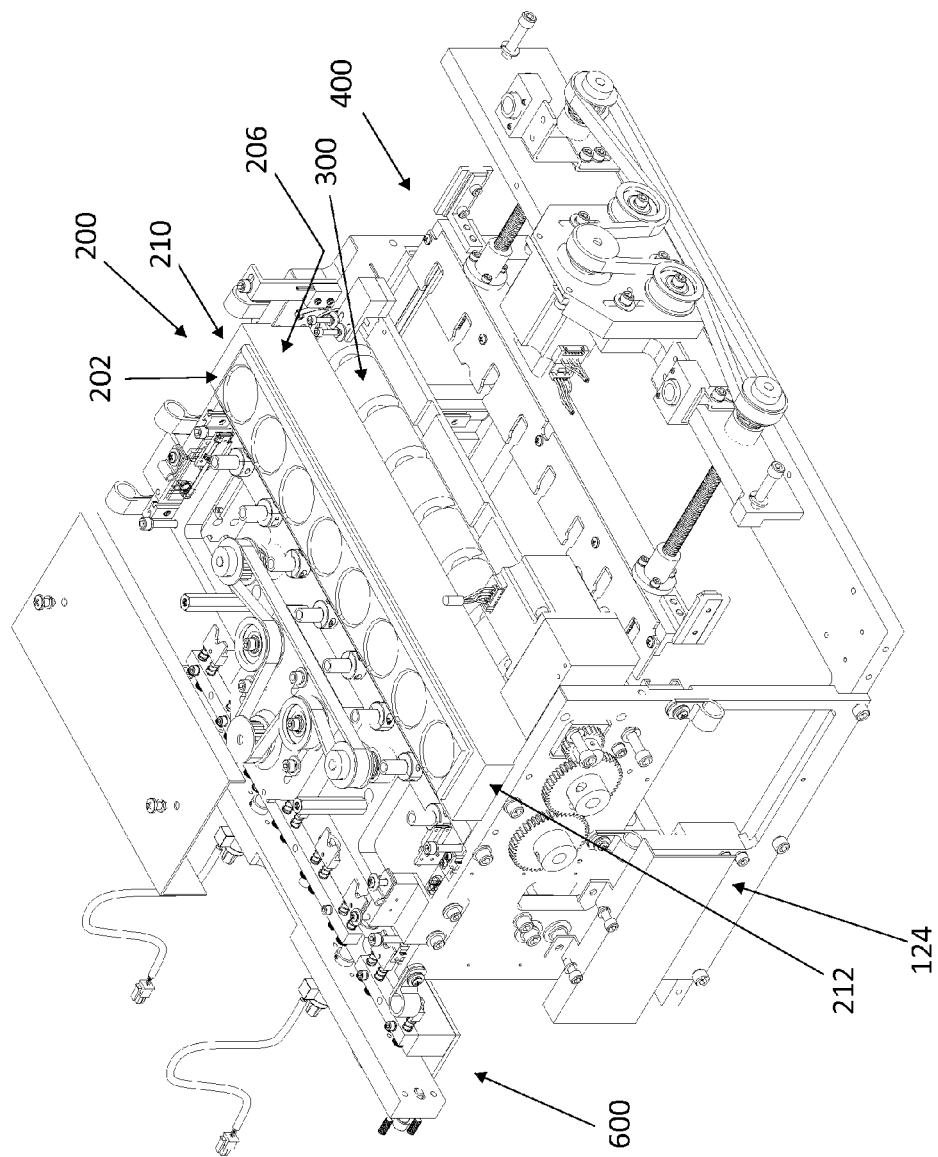
FIG. 2 shows a front, perspective view of an embodiment of the present invention with the housing removed.
Figure 3:
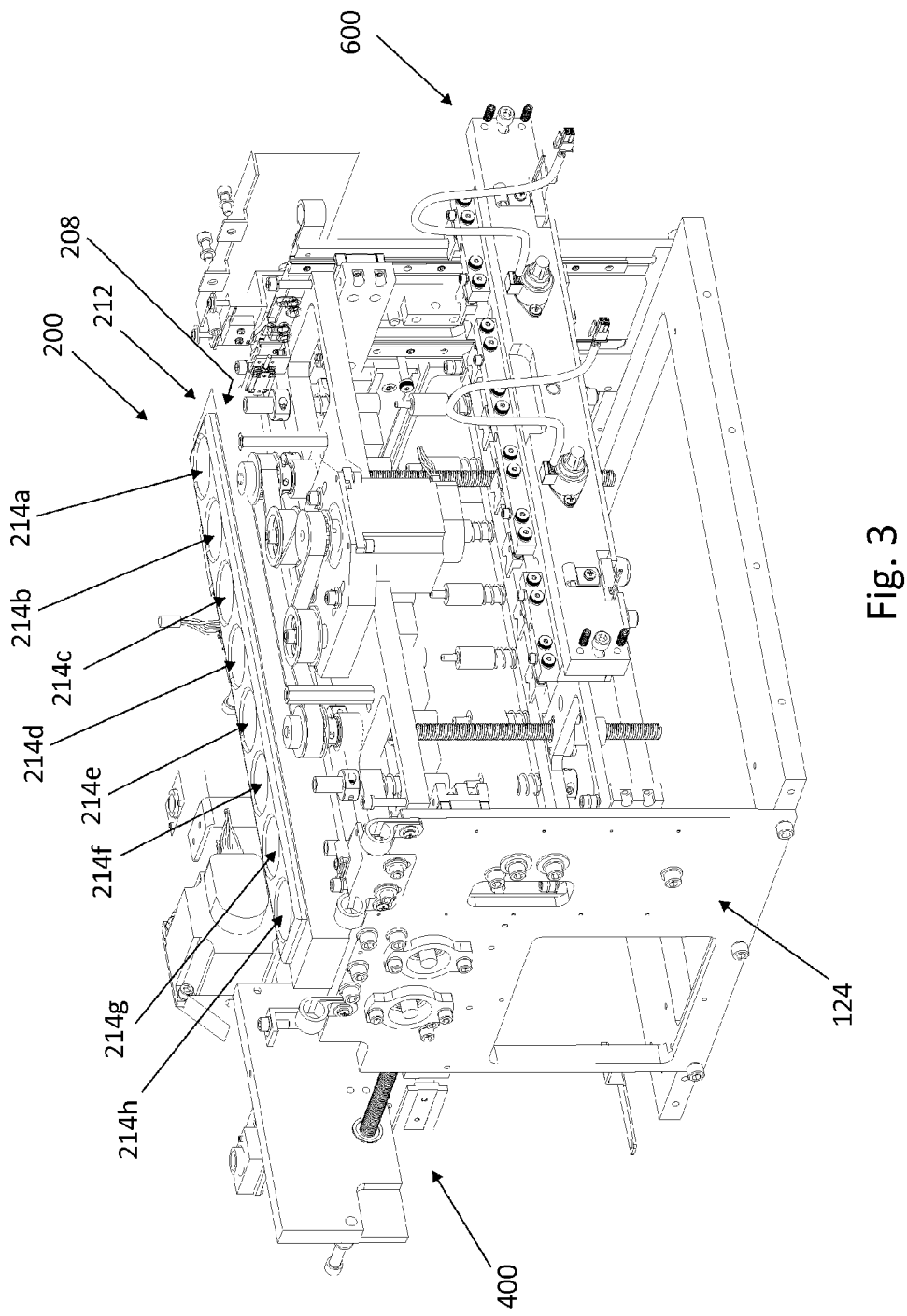
FIG. 3 shows a rear, perspective view of an embodiment of the present invention with the housing removed.

As shown in FIGS. 1-3, the automated filter changing system 100 of the present invention comprises a housing 102, a filter stack block 200 mounted on the housing 102, a filter separator 300 positioned below the filter stack block 200, and a shuttle plate 400 positioned below the filter separator 300. In general, filter stacks 10 are fed into the housing 102 through the filter stack block 200. From the filter stack block 200, the filters are separated into single filters 12 by the filter separator 300. The filter separator 300 transfers the filters 12 separated from their respective stacks (separated filters) to the shuttle plate 400. The shuttle plate 400 transfers the separated filters 12 to fluid couplers 500. Each fluid coupler 500 can connect to one separated filter 12 to create a fluidic path that utilizes the separated filter 12. A centering plate assembly 600 is used to facilitate proper alignment of the filters with the fluid coupler 500. A sample fluid to be measured or characterized can now be filtered as the fluid flows through the fluidic path from, for example, a dissolution machine to a measuring or collection device.

Housing

As shown in FIG. 1, the housing comprises a top 104, a bottom 106 opposite the top 104, a front 108 adjacent to the top 104 and bottom 106, a back 110 opposite the front 108 and adjacent to the top 104 and bottom 106, two opposing sides 112, 114 adjacent to the top 104, bottom 106, front 108 and back 110, and an underlying framework 124 upon which the various components can be mounted. In the preferred embodiment, the overall dimensions of the housing 102 have been minimized to fit on a workbench having a depth of approximately 24 inches. The front 108 of the housing comprises a collection bin 116 that can slide in and out of the housing 152. Discarded filters are collected in the collection bin 116. Preferably, the collection bin 116 has a see-through front panel so that discarded filters can be seen. The automated filter changer 100 may be operatively connected to a dissolution automated sampling machine that can pump fluids from the dissolution machine through the automated filter changer 100 and to a collection or measuring device. Therefore, tubing lines from the dissolution machine may be connected to the fluid coupler 500 of the automated filter changer 100 as described below. Tubing lines may be outside of the housing 102 and at a central location so that connecting the tubing from the dissolution device is made easy. As such, the automated filter changer 100 may be a part of an overall dissolution system.

A monitor 118 may be mounted on the housing 102 to display a graphic user interface to allow the user to interact with the automated filter changer 100. Various indicators 120 may be presented on the housing 102 to notify the user of the current status of the machine, including information such as errors, malfunctions, stoppages, normal operation, and the like. The same or more detailed information may be presented on the monitor 118. Various communication ports 122 may also be present on the housing to allow the automated filter changer to communicate with auxiliary devices, such as external monitors, input/output devices, USB drives, printers, other computers and servers, and the like. The monitor 118, indicators 120, and communication ports 122, as well as the various components described herein, may all be operatively associated with a computer 1000 for automatically operating the automated filter changer 100.

In some embodiments, the automated filter changer 100 may comprise a plurality of filter tubes 216a-h as shown in FIG. 1. The filter tubes 216a-h may be elongated, cylindrical tubes with openings 218a-h, 220a-h at opposite ends. Each filter tube 216a-h is configured to fit inside one of the plurality of holes 214a-h in the filter stack block 200. A portion of each tube 216a-h is inserted into one of the holes 214a-h of the filter stack block 200, while the remainder of each tube 216a-h projects out above the filter stack block 200. A filter stack 10a-h can be slid into each filter tube 216a-h through their respective top openings 218a-h. During use, filters 12 are released from their respective stacks 10a-h through the bottom openings 220a-h of each filter tube 216a-h. The filter tubes 216a-h, therefore, may provide some stability to the filter stacks 10a-h to maintain the filter stacks 10a-h in a vertical orientation. In addition, the filter tubes 216a-h provide some protection and coverage to the filters 12 to help keep the filters 12 clean or sterile. Preferably, the filter tubes 216a-h are transparent or see-through so that the filter stacks 10a-h therein are visible to the user. This allows the user to determine whether the filters 12 are still in the proper orientation to be fed into the filter separator 300. Preferably, the filter tubes 216a-h are designed to contain up to 25 filters each.

As shown in FIG. 2, the filter stack block 200 is connected to the housing 102, and in particular, to the framework 124, preferably at the top 104. The filter stack block 200 is generally rectangular or block shaped having a top 202, a bottom 204 opposite the top 202, a front 206 adjacent to the top 202 and bottom 204, a back 208 opposite the front 206 and adjacent to the top 202 and bottom 204, and two opposing sides 210, 212 adjacent to the top 202, bottom 204, front 206 and back 208. At least one hole 214a is formed through the top 202 and bottom 204. Preferably, a plurality of holes 214a-h are formed from the top 202 and through the bottom 204 and are arranged linearly from one side 210 to the opposite side 212 to create a row. In the preferred embodiment, 6 to 8 holes 214a-h are formed to accommodate 6 to 8 filter stacks 10a-h.

The holes 214a-h of the filter stack block 200 are configured to receive a plurality of filters 12 stacked one on top of another (i.e. the filter stacks 10a-h), wherein each hole 214a-h is configured to receive one filter stack 10. With reference to the single column shown in FIGS. 9A-9I (although the following description is applicable to all the columns), each filter 12 in a filter stack 10 comprises an inlet 14 and an outlet 16 opposite the inlet 14 with a filter body 18 therebetween. The filter body 18 contains a filtering mechanism, such as PTFE, PVDF, nylon, glass fiber membranes, and the like, to filter a fluid passing from the inlet 14 through the outlet 16. The inlet 14 and the outlet 16 are generally coaxially aligned along a central axis A that passes through the center of the filter body 18.

The filters 12 may be like those of a general syringe filter having a circular filter body 18, such as the 25 mm syringe filters. The inlet 14 may have a Luer lock feature. The outlet 16 may have an outer diameter 20 that is narrower than an inner diameter of the inlet 14. In some embodiments the outlet 16 may taper as it moves away from the filter body 18. Therefore, a plurality of filters 12 can be stacked linearly by inserting the outlet 16 of one filter 12 into the inlet 14 of another filter 12 to create the filter stack 10. In some embodiments, since the outlet 16 is tapered, it may be wedged into the inlet 14 of another filter 12 to create a resistance fit.

Filter Separator

Figure 4A:
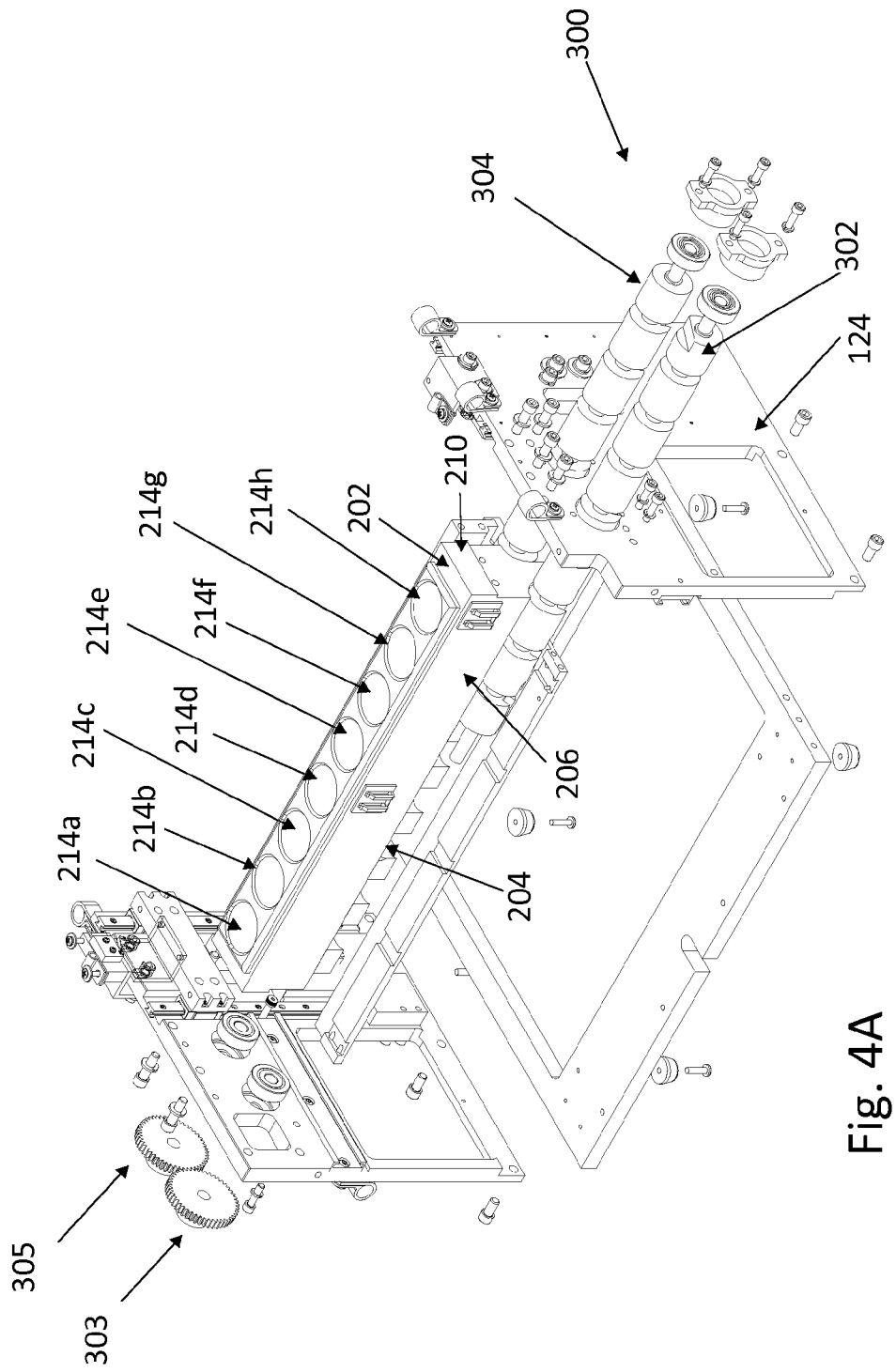
FIG. 4A shows a perspective view of an embodiment of the filter stack block and the separator, with various components removed for clarity.
Figure 4B:
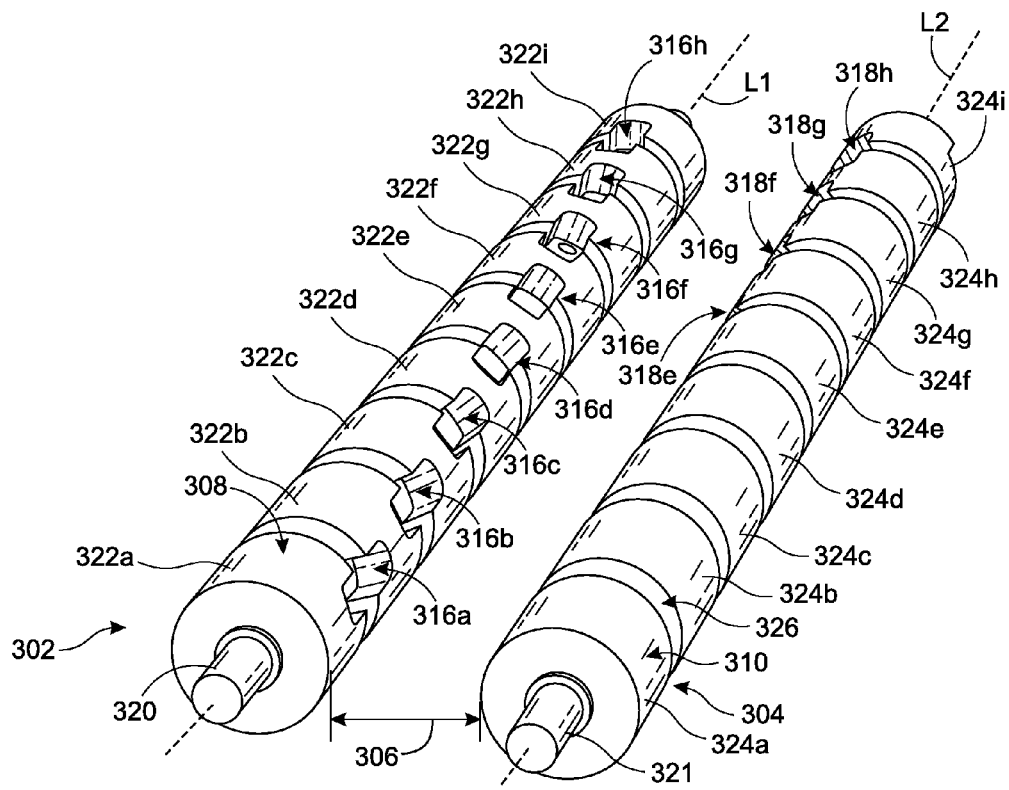
FIG. 4B shows a perspective view of an embodiment of the separator.
Figure 4C:
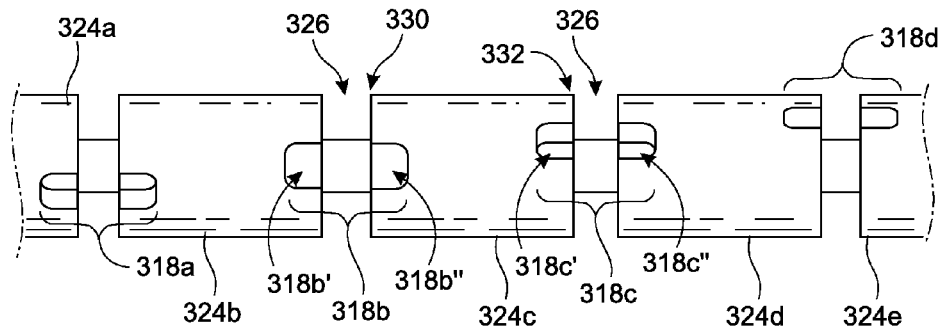
FIG. 4C shows an elevation view of a portion of one of the rollers of the separator.

Referring to FIGS. 4A-4C, in the preferred embodiment, the filter separator 300 is mounted on the framework 124 and positioned below the filter stack block 200 to separate one filter 12 at a time from each filter stack 10a-h in a sequential manner so that the first filter from a first stack is separated from the first stack before the first filter of a second stack is separated from the second stack, and so on. The first filter available for separation from the filter stack is referred to as the lead filter. Therefore, each column of filter stacks 10a-h will have a lead filter. In the arrangement discussed above, the lead filter is the bottom filter since separation occurs at the bottom of the stack. The separator 300 can be configured to have the lead filters in each column separated simultaneously. However, to reduce the amount of power and torque required, the filter separator 300 may be configured to separate one filter 12 from each column sequentially. Therefore, at any given time, only one filter 12 is being separated from its respective filter stack 10.

To achieve the single filter separation, in the preferred embodiment, the filter separator 300 comprises a pair of rollers 302, 304 that run substantially the width of the housing 102 from one side 112 to the other side 114. In the preferred embodiment, each roller 302, 304 is generally cylindrical in shape having an outer surface 308, 310 and defining a longitudinal axis L1, L2. The two rollers 302, 304 are arranged parallel to each other in a horizontal plane and are separated from each other by a gap 306 defined by the outer surfaces 308, 310 of each roller 302, 304. The gap 306 distance is smaller than the diameter 20 of the filter body 18. Therefore, when a filter stack 10 is placed into a hole 214a of the filter stack block 200, the filter stack 10a falls through the hole 214a until it rests on top of the pair of rollers 302, 304. This occurs for each filter stack 10a-h. Depending on the orientation of the filter 12, either the filter inlet 14 or the filter outlet 16 projects into the gap 306. In the preferred embodiment using standard filters, the inlet 14 or the female end may be pointed down into the gap 306 as shown in FIG. 9A.

Figure 9A:
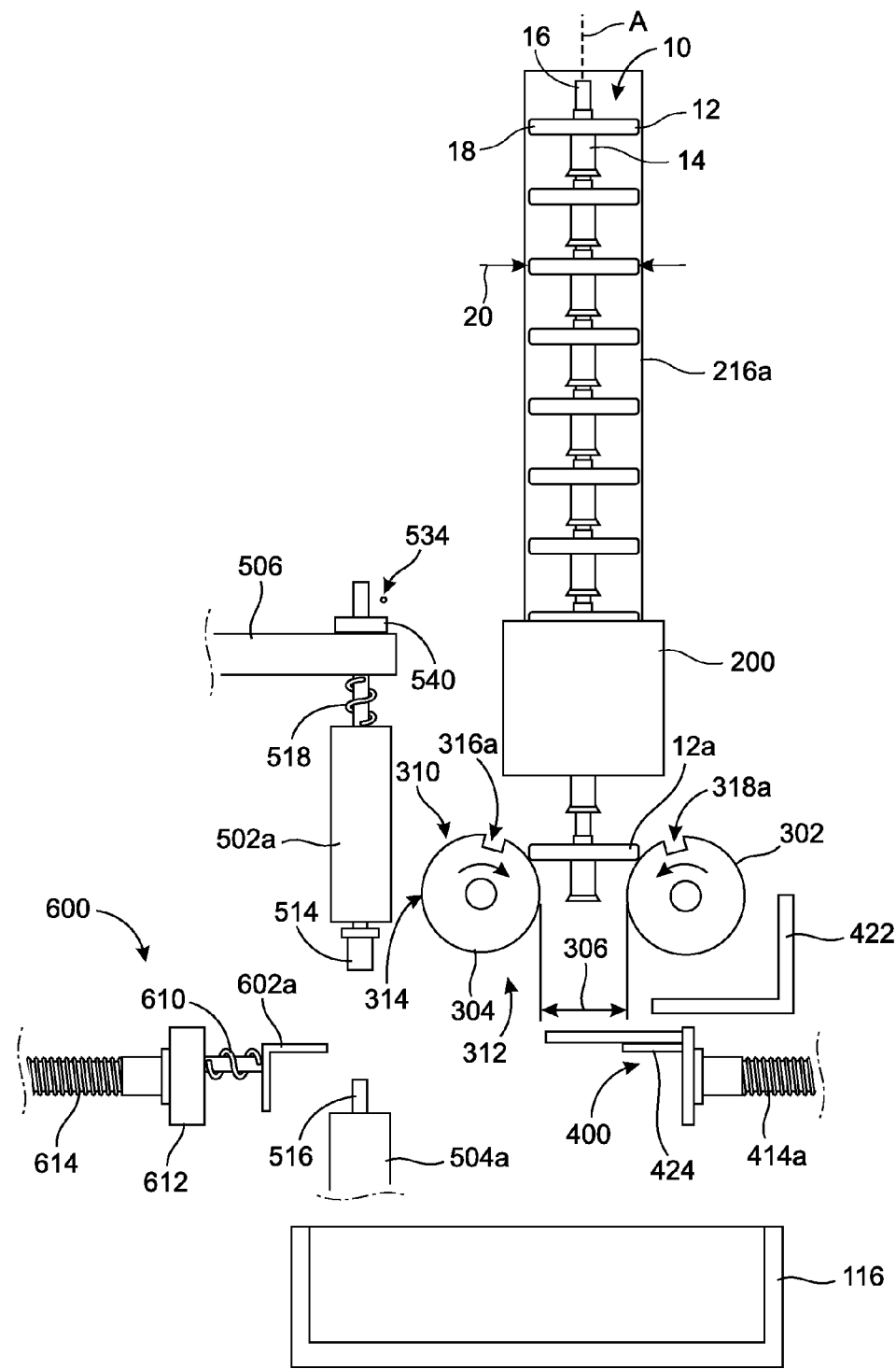
FIGS. 9A through 9I show the process of removing the filter from the filter stack using the present invention.
Figure 9B:
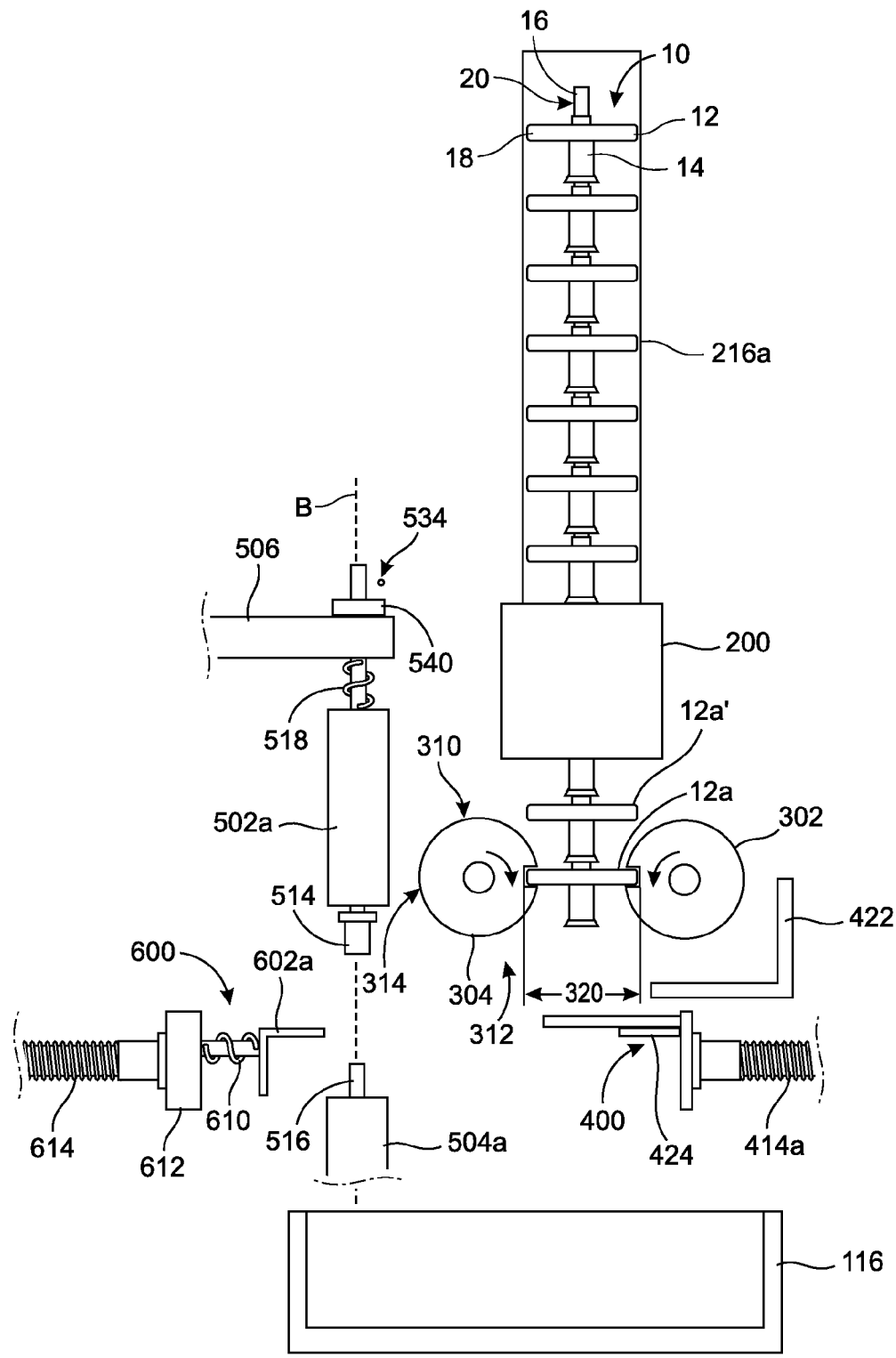

The roller pairs 302, 304 are configured to rotate about their respective longitudinal axes L1, L2 but in opposite directions as shown by the arrows in FIGS. 9A and 9B. Therefore, one roller 302 will rotate about its longitudinal axis L1 in a counterclockwise direction, and the second roller 304 will rotate about its longitudinal axis L2 in a clockwise direction. The rotation of both rollers 302, 304 is such that indentations 316a-h, 318a-h on the surface of the roller rotates from the top side 310 into the gap 306, then to the bottom side 312, then to the outer side 314 then back to the top side 310 again. Gears 303, 305 attached to a motor may be used to rotate the rollers 302, 304. The gears 303, 305 may be operatively connected to each other so that the rollers move simultaneously.

With reference to FIG. 4B, to separate the lead filter 12a from its filter stack 10 and allow the lead filter 12a to fall past the rollers 302, 304, each roller 302, 304 comprises at least one indentation 316a, 318a, respectively. In the preferred embodiment, each roller 302, 304 comprises a plurality of indentations 316a-h, 318a-h, respectively, to correspond with each column of filter stacks 10a-h. Furthermore, each indentation 316a-h on one roller 302 corresponds with an indentation 318a-h on the other roller 304 to form a matching indentation pair. In the preferred embodiment, the rollers 302, 304 comprise a plurality of matching indentation pairs such that the indentations 316a, 318a of each matching indentation pair face each other in the gap 306 during rotation of the rollers 302, 304 as shown in FIG. 9B. Therefore, the pair of rollers 302, 304 is configured so that as each roller 302, 304 rotates in opposite directions, the matching indentation pairs 316a-h, 318a-h align with and face each other as they pass through the gap 306.

As the indentations in the matching indentation pair align with each other within the gap 306, the gap size is temporarily enlarged (referred to as the enlarged gap 320) because the enlarged gap 320 distance is now defined by the walls of the indentations rather than the outer surface of the rollers. Preferably, the enlarged gap 320 is large enough such that when a filter 12 is seated within a matching indentation pair, the filter 12 is able to pass in between the rollers 302, 304.

Figure 9C:
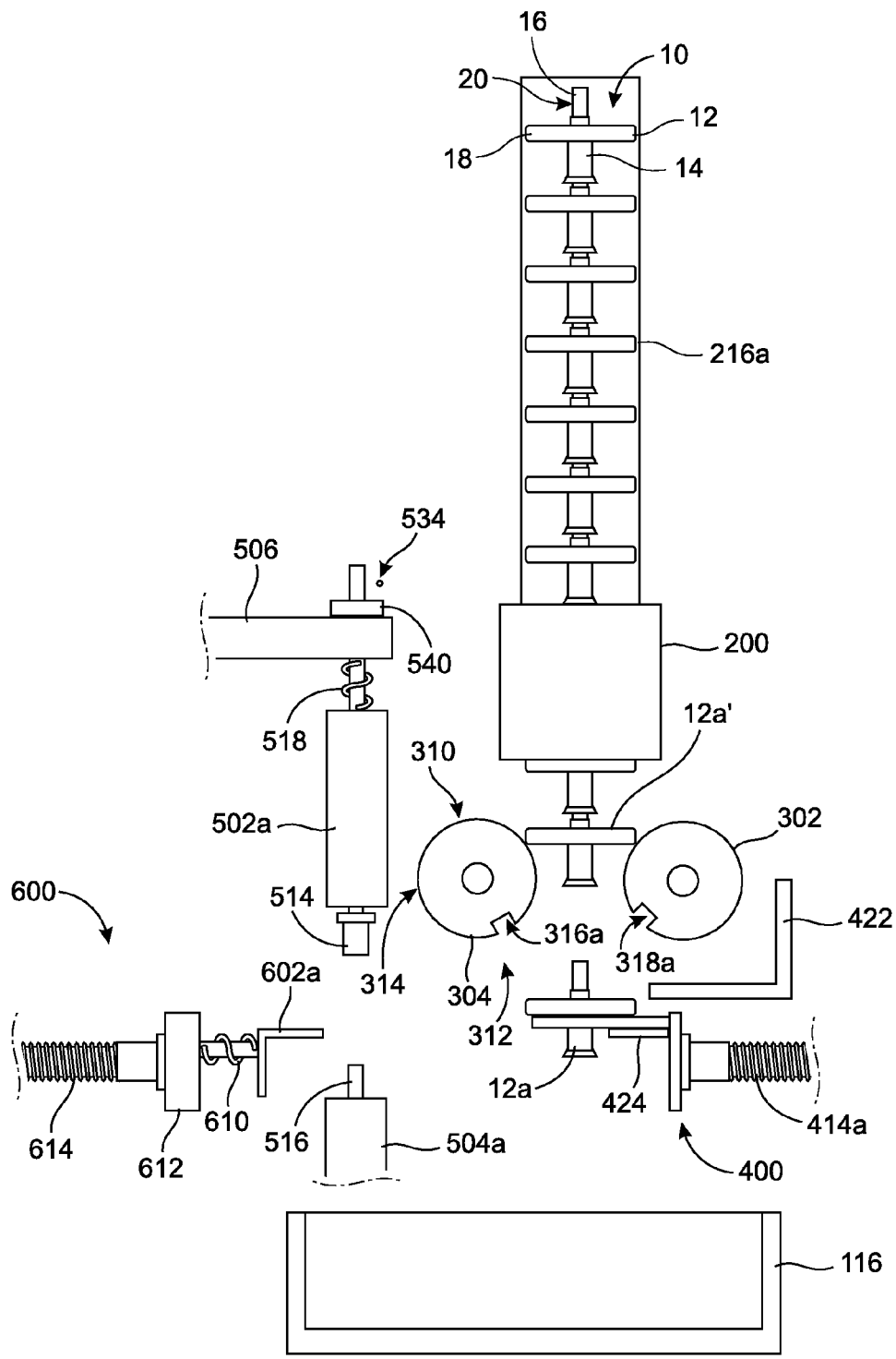
Figure 9D:
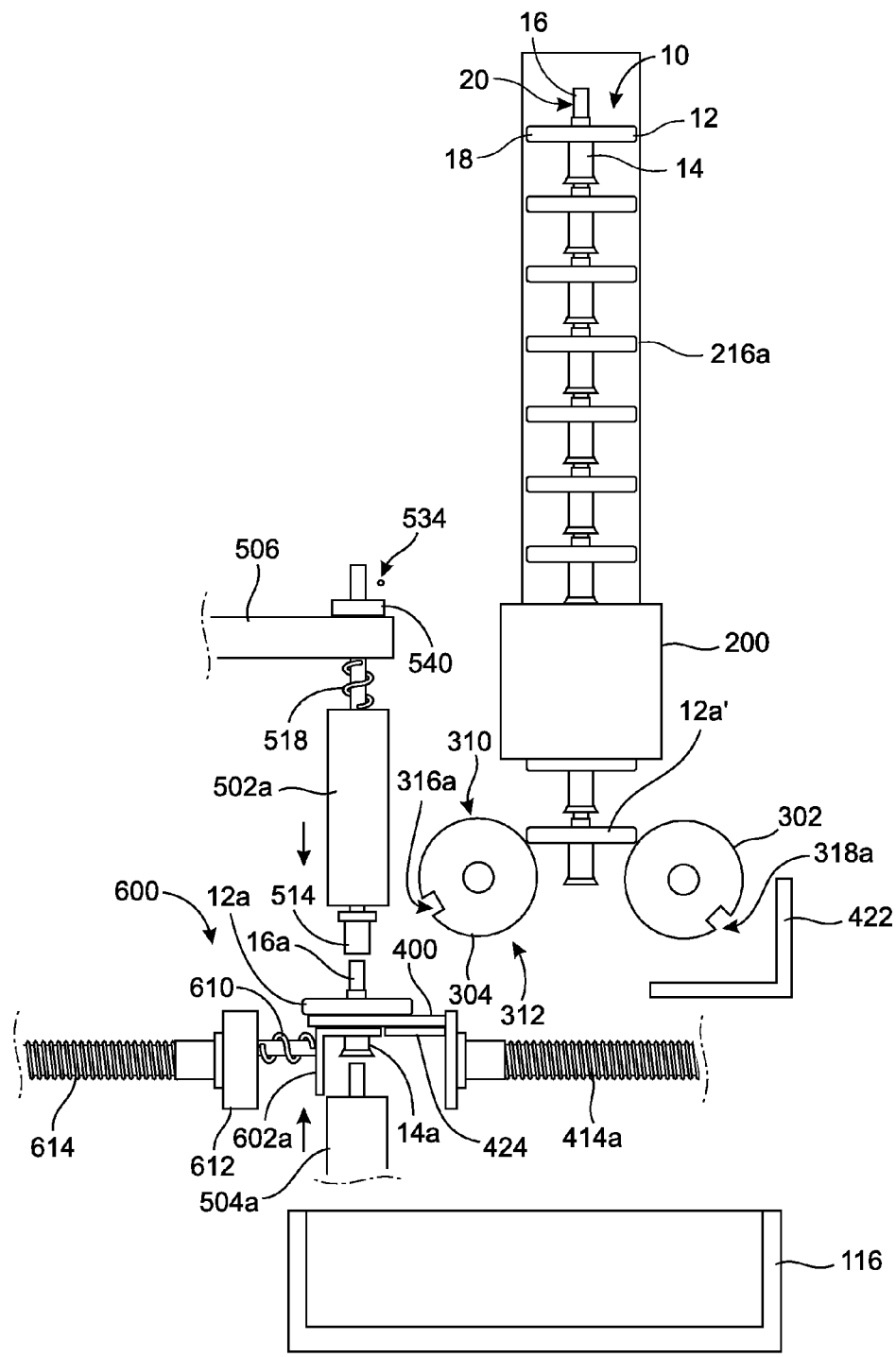
Figure 9E:
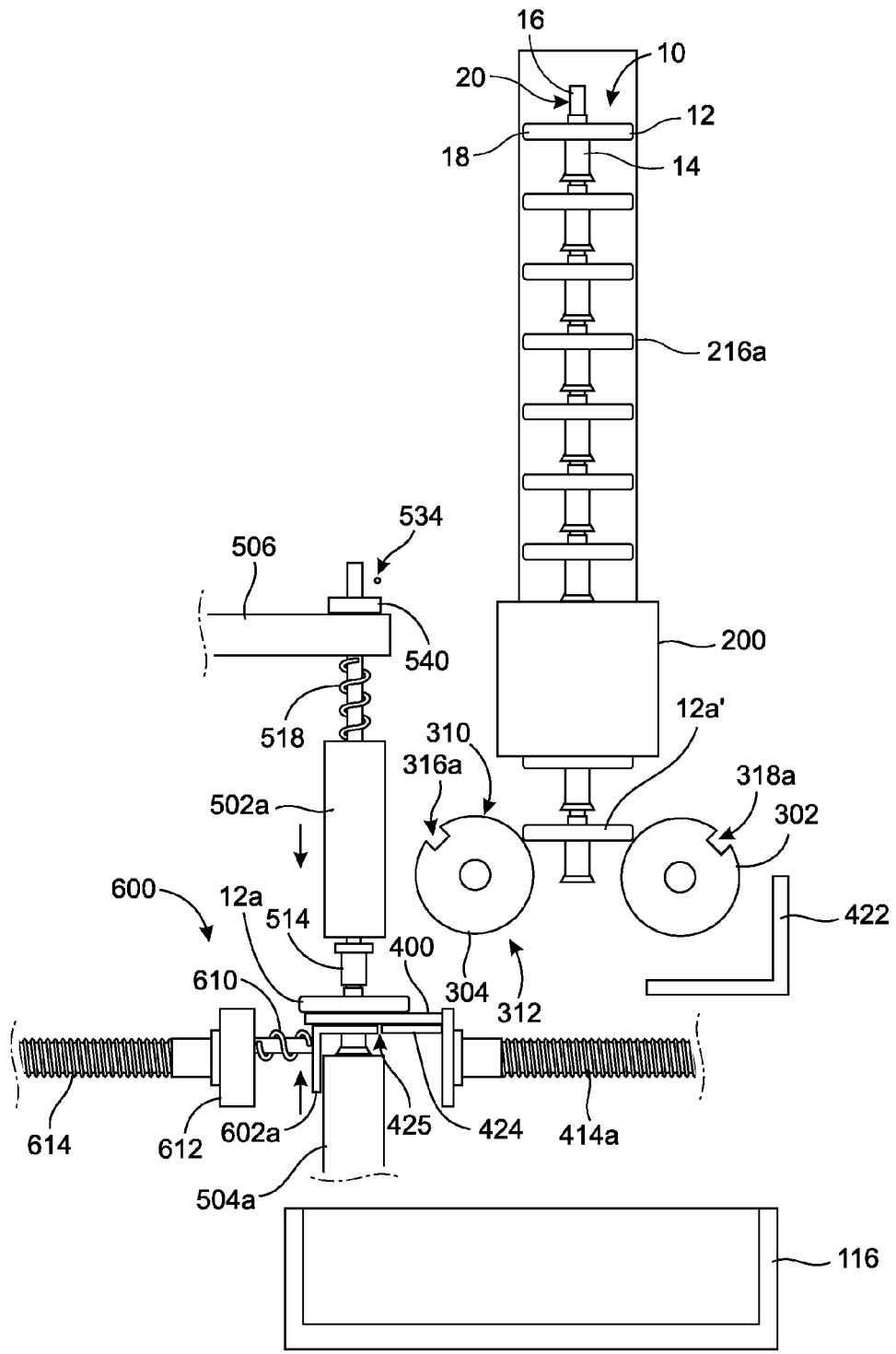
Figure 9F:
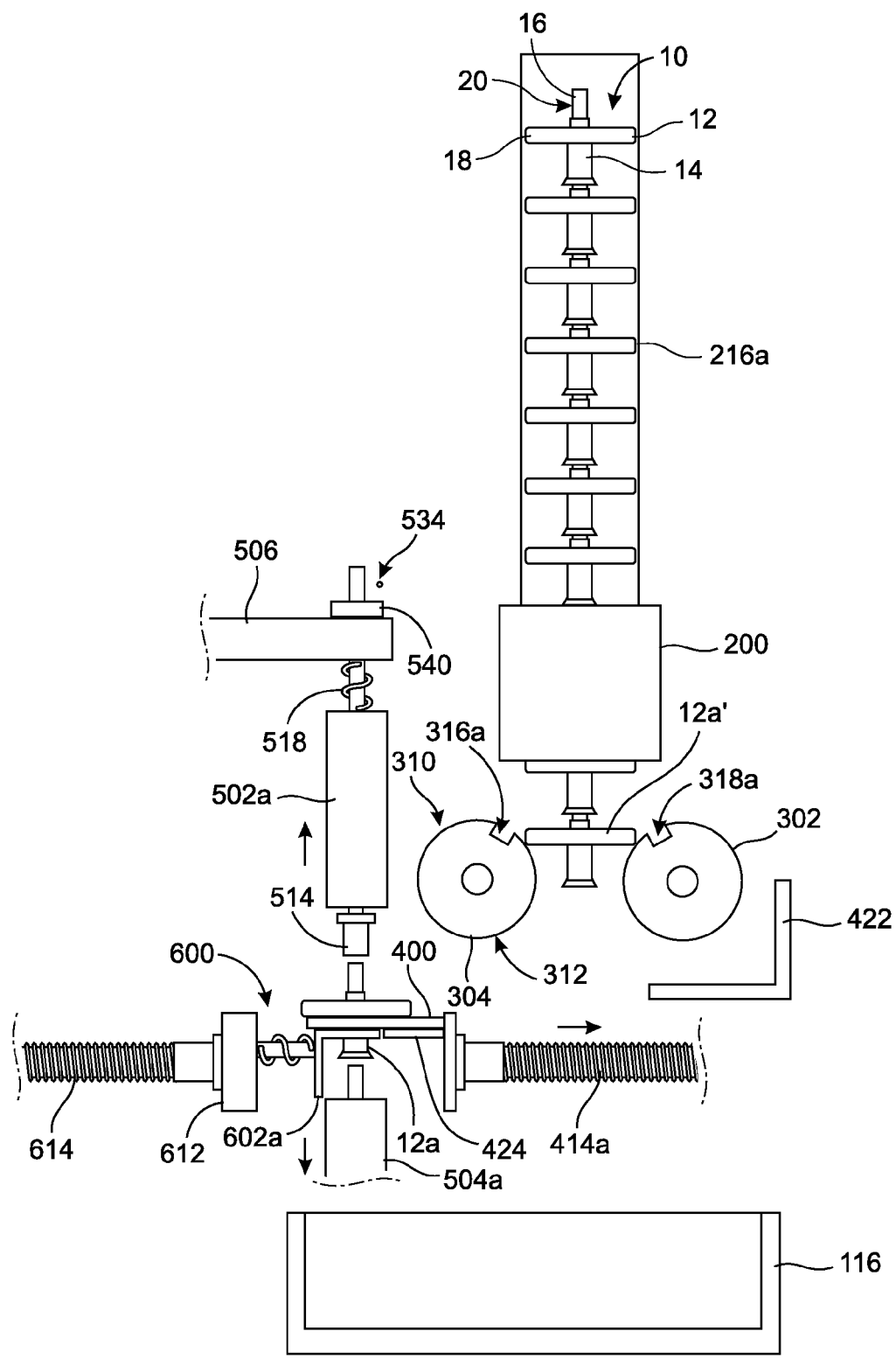
Figure 9G:
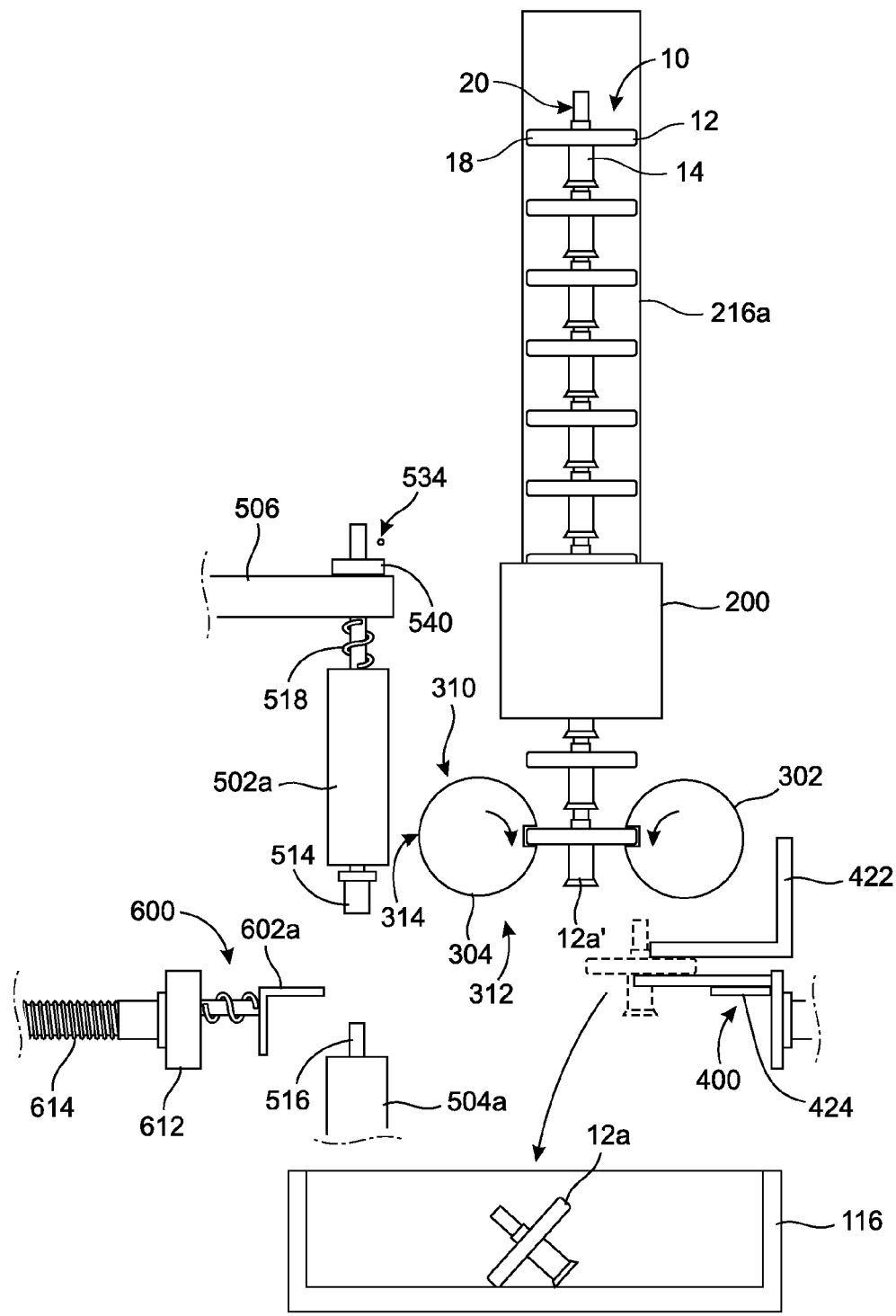

With reference to FIGS. 9A-9C, at the top side 310, the matching indentation pair 316a, 318a receives the lead filter 12a. As the rollers 302, 304 continue their rotation, the matching indentation pair rotates into the gap 306. Since the gap 306 has been enlarged due to the matching indentation pair, the filter moves into the enlarged gap 320. In the meanwhile, the next filter 12a' in line abuts against the outer surface 308, 310 of the rollers 302, 304 since the gap 306 in between the rollers 302, 304 is too small for the filter 12a' to fit through. Therefore, the lead filter 12a is separated from the rest of the filter stack 10 becoming a separated filter. Then as the matching indentation pair 316a, 318a moves towards the bottom side 312, the separated filter drops by the force of gravity while the filter stack 10 remains on the top side 310 of the rollers 302, 304. When the matching indentation pair reaches the top side 310 again, the next filter 12a' in the column is received into the indentations 316a, 318a and separated from the filter stack 10 in the same way and passed through the rollers 302, 304, as shown in FIGS. 9F and 9G. The matching indentation pair 316a, 318a can be moved to the top side 310 by continuing the rotation of the rollers or by reversing the rotation of the rollers. In the preferred embodiment, due to the configuration of the indentations 316a-h, 318a-h, after the lead filter 12a is separated, but before the next filter 12a' is separated, the lead filters in each of the other filter stacks 10b-h are separated in series.

In the preferred embodiment, in order for the filters from each column to be separated in series, each indentation 316a-h on the first roller 302 may be angularly offset about the longitudinal axis L1 of the first roller 302 from every other indentation 316a-h on the first roller 302. Similarly, each indentation 318a-h on the second roller 304 may be angularly offset about the longitudinal axis L2 of the second roller 304 from every other indentation 318a-h on the second roller 304. The degree of the angular offset in between each indentation in the first roller 302 is the same as the degree of angular offset in between each indentation in the second roller 304, except that the angular offset is in opposite directions. Therefore, when a matching indentation pair 316a, 318a is aligned in the gap, a mirror image is created between the two rollers 302, 304; however, due to the angular offsets, no other matching indentation pair 316b-h, 318b-h is aligned in the gap 306 at the same time as another matching indentation pair. The degree of angular offset between any adjacent indentation pair may range from approximately 2 degrees to approximately 60 degrees. In some embodiments, the angular offset ranges from 5 degrees to 45 degrees. Preferably, the angular offset is approximately 30 degrees or less. In some embodiments, the angular offset is approximately 25 degrees or less. The minimum angular degree of offset is determined by the amount of space needed between adjacent matching indentation pairs that allow one filter to be separated from its filter stack at any given time.

What follows is that no matching indentation pair is receiving a lead filter from its respective filter stack at the same time as another matching indentation pair. Since the pair of rollers are configured to rotate in opposite direction about their respective longitudinal axes each matching indentation pair will eventually receive a lead filter, but it will do so sequentially or in series, and not simultaneously. Specifically, during rotation of the pair of rollers, a first matching indentation pair 316a, 318a will receive a lead filter 12, then as the first matching indentation pair 316a, 318a separates the lead filter 12 from its filter stack 10a, the next matching indentation pair 316b, 318b will receive a lead filter 12 from the next column of filter stacks 10b in the row, and as this indentation pair 316b, 318b separates the lead filter 12 from its filter stack 10b, subsequent indentation pairs 316c-h, 318c-h will receive lead filters 12 from the subsequent columns of filter stacks 10c-h, and so on. This arrangement of matching indentation pairs allows only one filter to be separated from any filter stack at a time. By having one filter removed from any filter stack at a time, less torque, and therefore, less power is required by the rollers.

As shown in FIG. 4B, in the preferred embodiment, each roller may comprise an elongated bar 320, 321 defining the longitudinal axes L1, L2, respectively, and a plurality of cylinders 322a-i, 324a-i, respectively, coaxially formed or mounted on their respective elongated bars 320, 321. Preferably, each roller 302, 304 has a first cylinder 322a, 324a, a last cylinder 322i, 324i, and a plurality of intermediate cylinders 322b-h, 324b-h in between their respective first cylinder 322a, 324a and last cylinder 322i, 324i. Referring to the example in FIG. 4C, each cylinder 322a-i, 324a-i is spaced apart from another so as to create a space 326 in between each cylinder. All of the cylinders 322a-i, 324a-i have a first end 330 and a second end 332. Each intermediate cylinder may comprise two indentations, one at the first end 330 and one at the second end 332, which are offset from each other, but align with indentations of another cylinder. By way of example only, the following description and FIG. 4C pertain to cylinders 324b, 324c, and 324d, but the principle applies to all of the intermediate cylinders.

The first indentation 318b" and the second indentation 318c' of intermediate cylinder 324c is angularly offset from each other about the longitudinal axis L2 as discussed above. The second indentation 318c' of intermediate cylinder 324c is in line with the first indentation 318c" of an immediately adjacent cylinder 324d to form the indentation 318c between two immediately adjacent cylinders 324c, 324d. An indentation 318c on one roller 304 has a matching indentation 316c on the other roller 302 to form the matching indentation pair as discussed above. Similarly, cylinder 324b has a first indentation 318a at its first end and a second indentation 318b' at its second end that is offset from the first indentation 318a. Cylinder 324c has a first indentation 318b" at its first end 330 that aligns with the indentation 318b'. These two indentations form indentation 318b, which corresponds with indentation 316b on roller 302. Therefore, in this embodiment, the matching indentation pair is created from four indentations on four different cylinders. As discussed above, due to the angular offset in the indentations, each matching indentation pair receives a lead filter in sequence rather than at the same time. This allows filters to be released sequentially, one at a time.

In this embodiment, three gaps exist between the two rollers. The first gap 306 is defined by the distance between the outer surfaces of the rollers. The second gap 320 is the extended gap as measured from indentation to indentation between matching indentation pairs. The third gap is defined by the distance between the elongated bars 320, 321 as measured at the space 326 in between the cylinders. The first gap 306 measured between the cylinder of the first roller 302 and the corresponding cylinder on the second roller 304 is smaller than the diameter 20 of the filter body 18. The third gap between the elongated bar 320 of the first roller 302 and the elongated bar 321 of the second roller 304 is larger than the diameter 20 of the filter body 18. The second gap 320 in between indentations of matching pairs is any size larger than the first gap and up to the size of the third gap.

In this embodiment, as shown in FIG. 9A-9C each filter stack 10 is aligned so that the central axis A falls in the gap 306, and is aligned in the space 326 in between two cylinders. In this configuration, the largest part of the filter body 18 aligns with the space 326 in between two cylinders, while adjacent portions of the filter body rest on the cylinders, thereby making a four-point contact. Then as the rollers 302, 304 rotate, eventually the filter 12a drops into the matching indentation pair 316a, 318a. As the rollers continues to rotate, the widest portion of the filter body 10 passes through the gap 306 due to the spacing 326 in between cylinders and the filter 12a is able to drop below the rollers 302, 304. Due to the angular offset of the matching indentation pairs, one filter falls at a time from each column sequentially.

In some embodiments, the rollers 302, 304 may be adjustable to change the gap distance to accommodate filters of different sizes.

The Shuttle Plate

When a filter 12 is separated from its filter stack 10 by the filter separator 300, the separated filter may drop to the shuttle plate 400. The shuttle plate 400 has multiple positions. In the first position, the shuttle plate 400 is positioned directly below the filter separator 300 (first position) to catch a separated filter.

Figure 5:
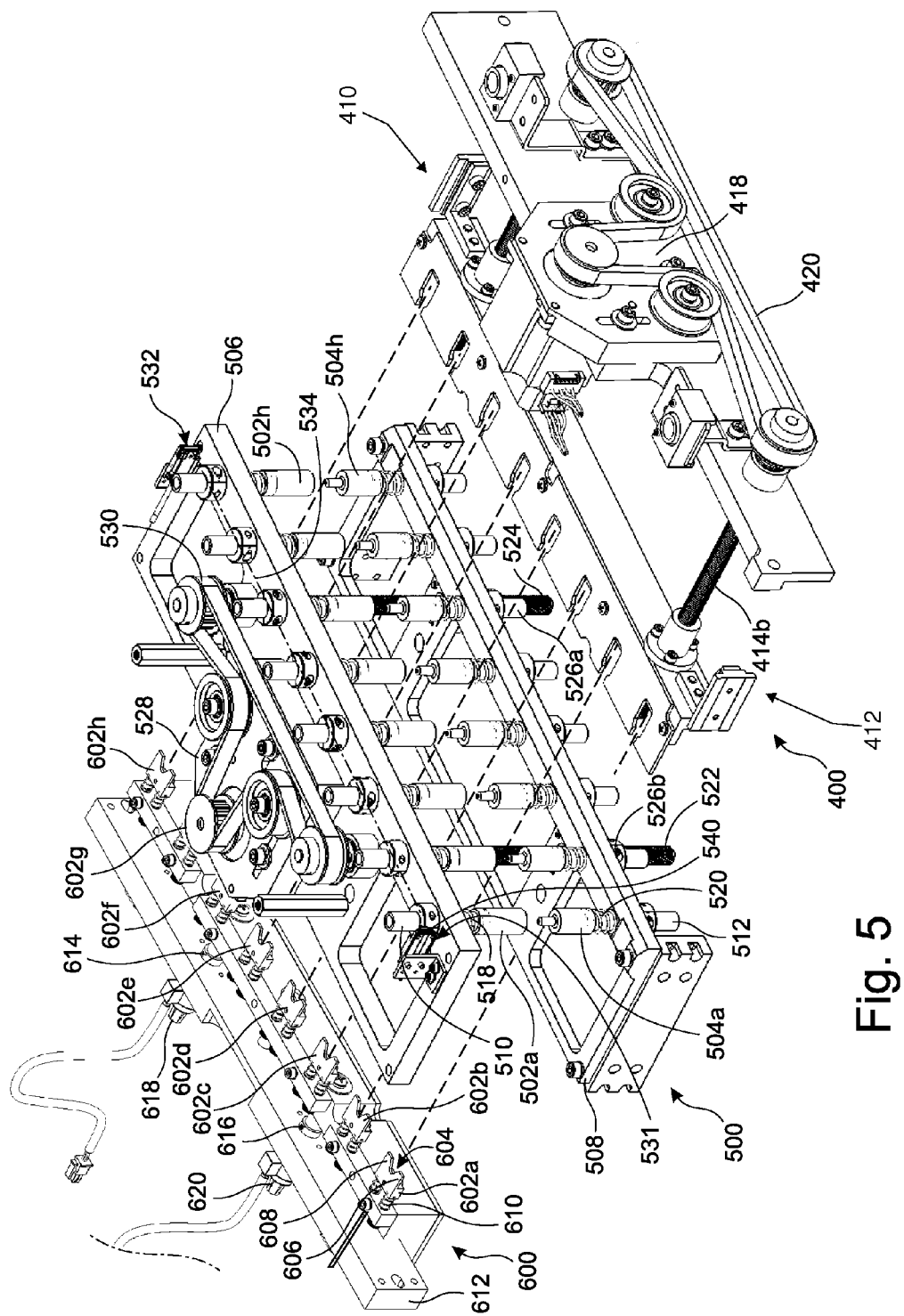
FIG. 5 shows a partially exploded view of an embodiment of the present invention with the housing removed.
Figure 6:
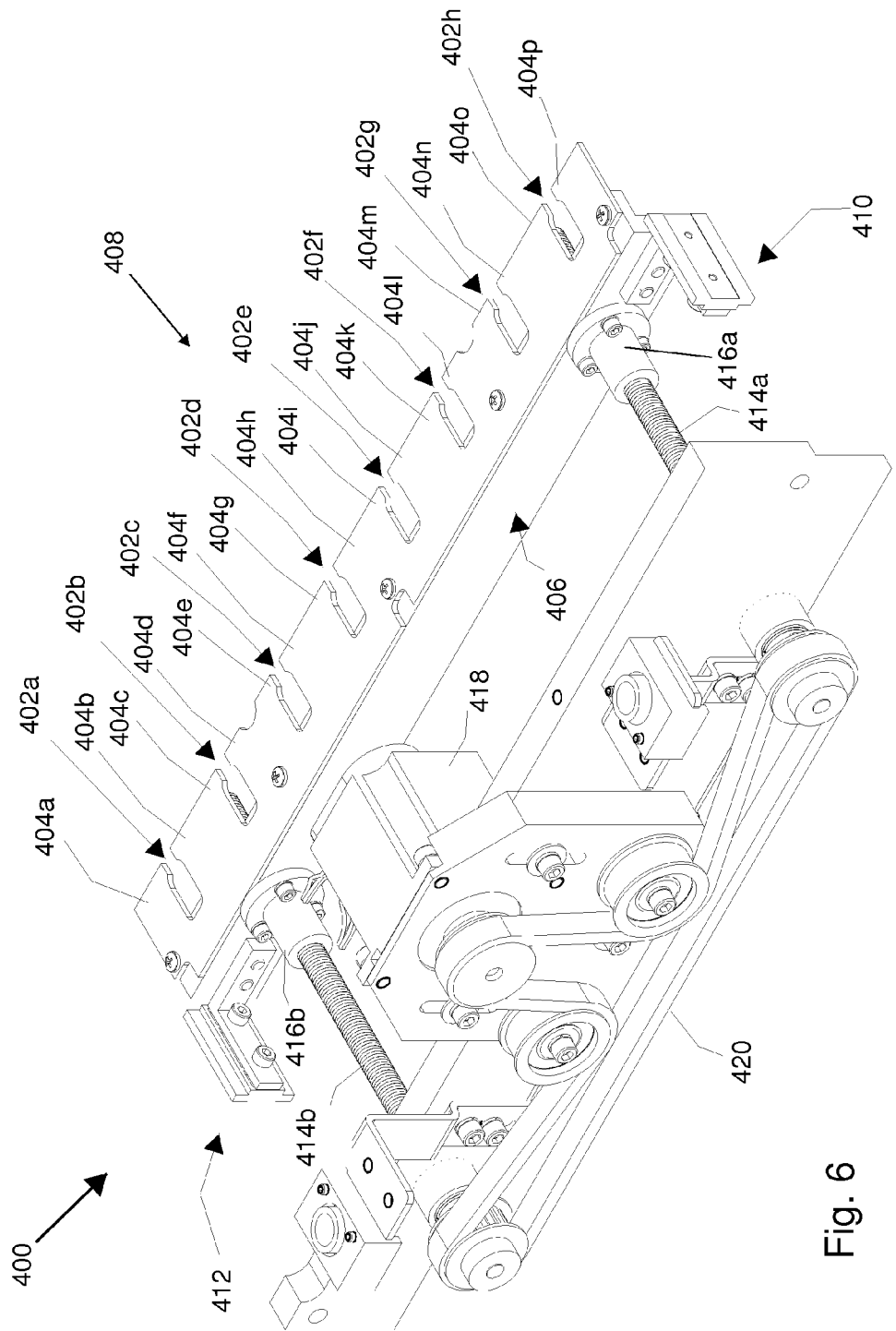
FIG. 6 shows a perspective view of an embodiment of the shuttle plate.

As shown in FIGS. 5-6, the shuttle plate 400 comprises a plurality of slots 402a-h defined by slot arms 404a-p, each slot 402a-h configured to align with one of the filter stacks 10a-h when the shuttle plate 400 is in the first position. The slot arms 404a-p are closed at one side 406, and open at the opposite side 408 so that the slot arms 404a-p form a "U"-shaped or "V"-shaped configuration. When the lead filter 12 drops onto the shuttle plate 400, the inlet 14 or outlet 16 of the filter 12 falls through one of the slots 402a-h and the filter body 18 rests against the shuttle plate 400 surface. In some embodiments, a predetermined amount of time may pass to allow the filter 12 to settle on the shuttle plate 400 before moving to the next step. In some embodiments, the shuttle plate 400 may jiggle or jostle to force the filter body 18 to settle on the shuttle plate 400 in the proper orientation.

In some embodiments, the paired slot arms that define a slot may taper inwardly either gradually or abruptly toward each other. For example, slot arms 404a, 404b, which define slot 402a taper toward each other so that the opening to the slot 402a is slightly narrower than the slot 402a itself, as shown in FIG. 6. The same applies to each of the other slot arm pairs. The narrowing of the opening to the slots 402a-h creates a restraint profile that improves the proper seating of the filter 12 once dropped into the shuttle plate 400.

The shuttle plate 400 is movable in a first horizontal direction to carry the released filter 12 or a set of released filters to a second position for connection to a fluid coupler 500. In the preferred embodiment, the shuttle plate 400 moves horizontally towards the back 110 of the housing 102 in this step. In the preferred embodiment, the shuttle plate 400 comprises 6 to 8 slots. To assure even movement, the shuttle plate 400 is attached to two linear slides 410, 412 located at each end of the shuttle plate 400. The two linear slides 410, 412 will be driven at each end by a lead screw 414a, 414b and nut 416a, 416b. The two screws will operate together for equal movement of the shuttle plate 400 at each end. A motor 418 will connect to one of the screws or will drive a belt 420 that is positioned midway between and operatively connected to the screws 414a, 414b to drive both screws 414a, 414b simultaneously in a forward or backward direction.

The Fluid Coupler

Figure 7:
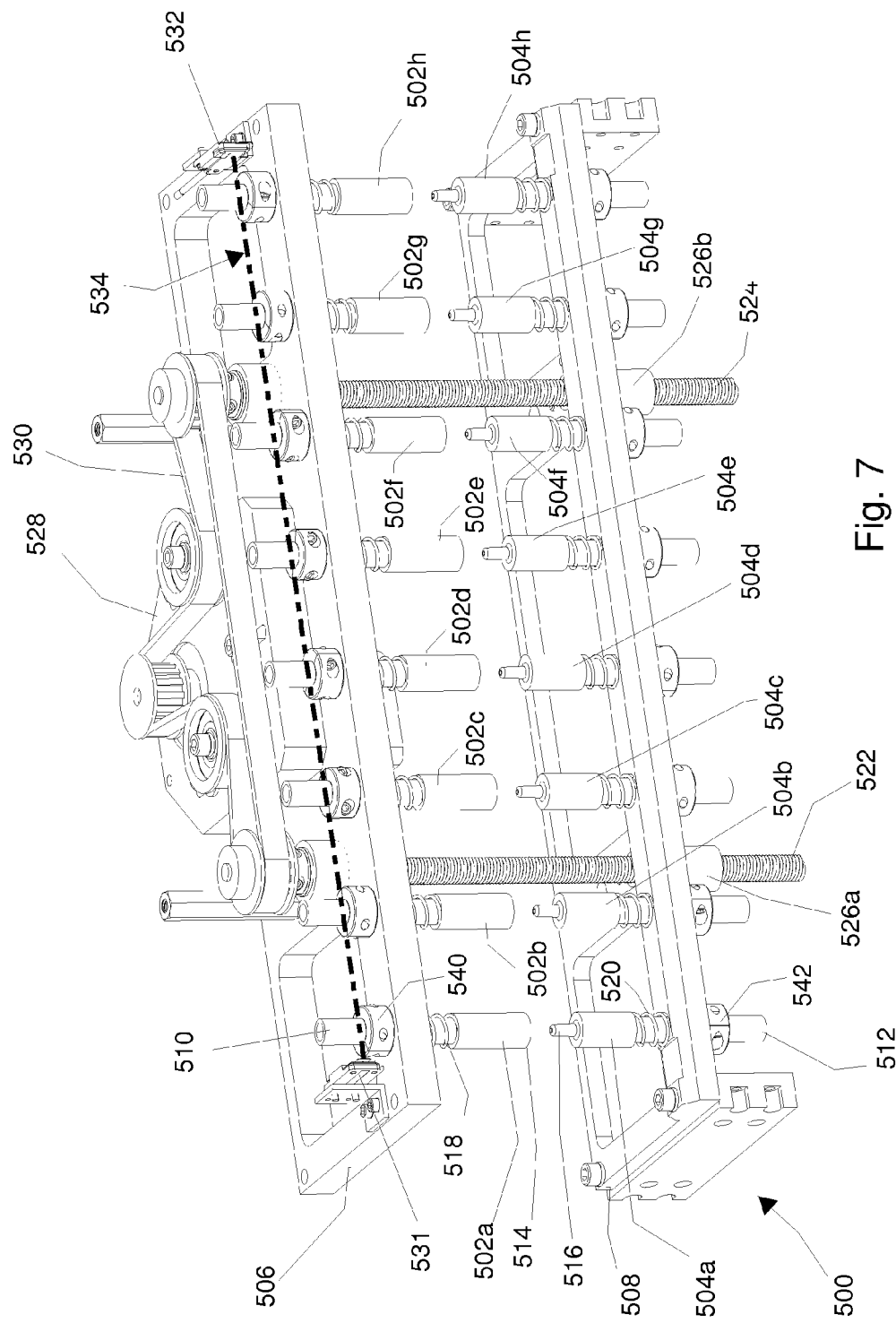
FIG. 7 shows a perspective view of an embodiment of the fluid coupler.

As shown in FIG. 7, the fluid coupler 500 comprises upper fluid couplings 502a-h and lower fluid couplings 504a-h, one lower fluid coupling coaxially aligned with one upper fluid coupling. Each upper fluid coupling 502a-h and lower fluid coupling 504a-h pair defines a vertical axis B and both can move up and down along the vertical axis B. The upper fluid couplings 502a-h and the lower fluid couplings 504a-h are mounted to movable bars (upper 506 and lower bars 508, respectively) that can move up and down to cause the upper fluid couplings 502a-h and the lower fluid couplings 504a-h to move towards and away from each other along their respective vertical axes B. Once the separated filter is trapped against the shuttle plate 400 and the centering plate assembly 600 (as discussed below), the fluid couplings 502a-h, 504a-h are actuated to move towards each other. Since the inlet 14 and the outlet 16 of the filter 12a is aligned with the vertical axis B and the fluid couplings 502a-h, 504a-h move along the vertical axis B, one of the upper and lower fluid coupling pairs 502a-h, 504a-h attach to the inlet 14 and the outlet 16 of the filter 12a to complete the fluidic path. Depending on the orientation of the filter 12a, the inlet 14 may be connected to one of the lower fluid couplings 504a-h and the outlet 16 may be connected to the corresponding upper fluid coupling 502a-h or vice versa.

In the preferred embodiment, each fluid coupling comprises a rod 510, 512 at the first end that connects to a tube, and a connector 514, 516 at the second end. To accommodate standard syringe filters having Luer lock connectors, one of the fluid couplings is a male connector and the other fluid coupling is a female connector. In the preferred embodiment, the filter 12a is positioned on the shuttle plate 400 with the female end projecting downwardly. Therefore, the lower fluid couplings 504a-h will have a male connector at its second end to be inserted into the female inlet 14 of the filter 12, and the upper fluid couplings 502a-h will have a female connector at its second end so that the male outlet 16 of the filter 12 can be inserted into the female connector of the upper fluid couplings 502a-h. The rods 510, 512 may be spring-loaded 518, 520 to allow for minor engagement variations when connecting to the filters.

The upper and lower bars 506, 508 will be driven vertically by lead screws 522, 524 coupled to each end of the bar area. Each screw 522, 524 may be fixed to the upper bar 506, although allowed to rotate, and then threaded through a nut 526a, 526b that is secured on the lower bar 508. The two screws 522, 524 may be coupled together for equal movement. A motor 528 may connect to one of the screws 522, 524 or may drive the belt 530 midway between the screws 522, 524. When activated the screws 522, 524 will drive each bar 506, 508 with the rods towards or away from each other. Incoming and outgoing fluid line connections to the rods 510, 512 will be available for easy access on the outside of the housing. In the preferred embodiment, all of the upper and lower fluid couplings 502a-h, 504a-h can either engage all filters at one time or no filters for straight through fluid flow without media filters. In some embodiments, some fluid couplers may have filters and some fluid couplers may not have filters.

In some embodiments, an optical emitter 531 and a detector 532 are mounted at opposite ends on the top side of the upper bar 506. The optical emitter 531 emits a beam 534 that is received by the detector 532 when the path of the beam 534 is unobstructed. The upper fluid couplings 502a-h are slidably mounted on the upper bar 506. The rods 510 (only one labeled for clarity, but each upper coupling 502a-h has one as shown in FIG. 7) may be spring-loaded 518 to bias the upper fluid couplings 502a-h in a first position. Mounted on each rod 510 of each upper fluid coupling 502a-h may be a collar 540 (only one labeled, but shown for each fluid coupling) that can move up and down with its respective fluid coupling 502a-h.

When the upper fluid couplings 502a-h are in their first position, the beam 534 remains unobstructed. When any one or more of the upper fluid couplings 502a-h are not properly inserted into their respective filters 12, the affected upper fluid coupling 502a-h may not move downwardly with the upper bar 506. As the upper bar 506 continues to move downwardly, the fluid coupling 502a-h does not move and is placed in a second position relative to the upper bar 506. Since the optical emitter is fixed to the upper bar 506, and the collar 540 is fixed to the upper fluid coupling 502a-h, the collar 540 moves into the path of the beam 534. The detector 532 no longer receives the beam 534, and sends a signal to the computer 1000 to indicate that at least one of the fluid couplings 502a-h is not properly connected with filter 12 and appropriate action can be taken. In some embodiments, the upper fluid couplings 502a-h may each have a collar 540 and/or the lower fluid couplings 504a-h may each have a collar 542, and the optical emitter 531 and detector 532 may be on the upper bar 506 and/or the lower bar 508 to perform the function described above.

In some embodiments, a fluid may be sampled without first being filtered. In such a situation, the lower coupling 504a-h and upper coupling 502a-h continue to move towards each other until they couple with each other to complete the fluidic path. In some embodiments, the centering plate assembly 600 may be retracted so as not to interfere with the coupling of the upper and lower fluid couplings 502a-h, 504a-h.

The Centering Plate

Figure 8:
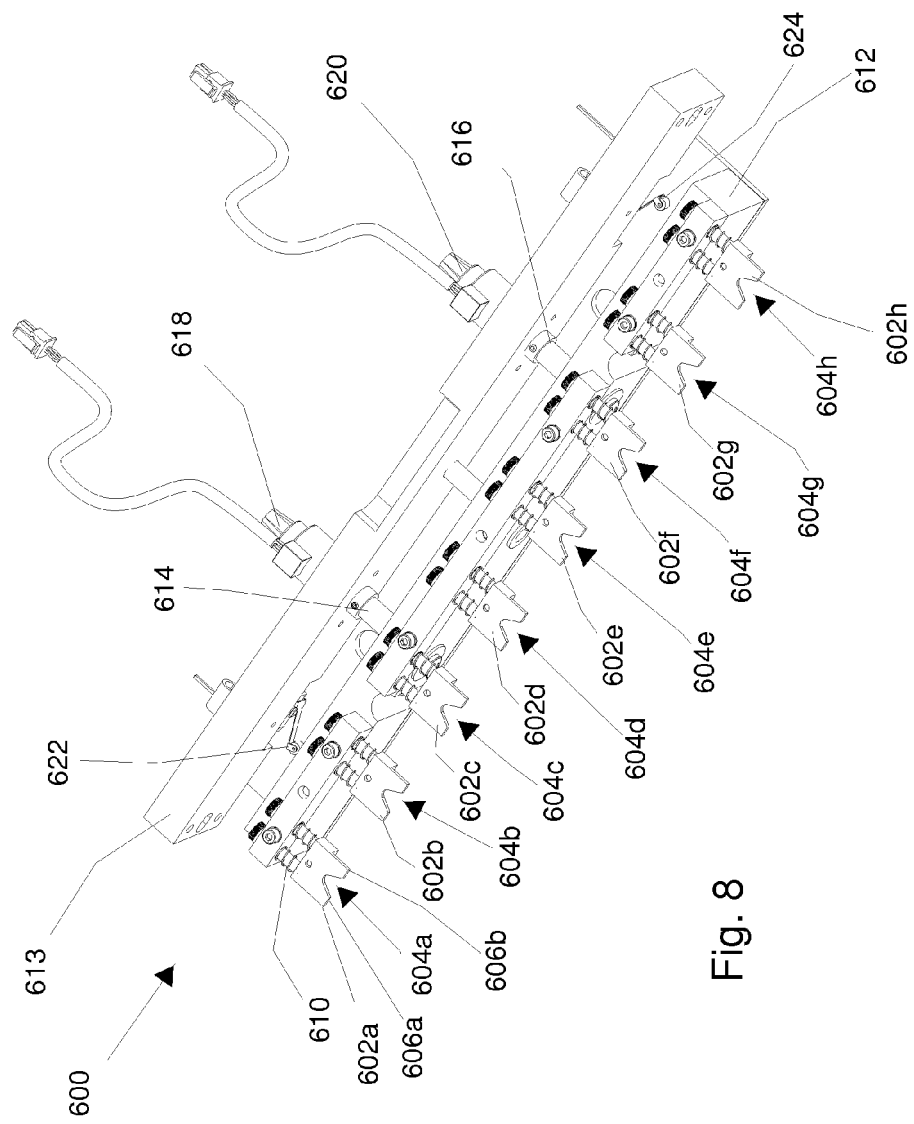
FIG. 8 shows a perspective view of an embodiment of the centering plate.

Located towards the back side 110 of the housing is a centering plate assembly 600 comprising one or more centering plates 602a-h as shown in FIG. 8. Each centering plate 602a-h is aligned with one fluid coupling 502a-h, 504a-h such that each centering plate 602a-h is in between one upper fluid coupling 502a-h and its respective lower fluid coupling 504a-h. Each centering plate 602a-h comprises a notch 604 defined by a pair of notch arms 606a, 606b (only two notch arms are labeled for the sake of clarity, but each centering plate has notch arms as shown, which are all characteristically the same). The notch arms 606a-p may be connected at one end and open at the opposite end forming a "U"-shaped or "V"-shaped notch. The opening of the notches of each center plate 602a-h and the opening of each slot 402a-h of the shuttle plate 400 face each other. Each notch 604a-h of the centering plate 600 is aligned with one slot 402a-h of the shuttle plate 400 such that when the shuttle plate 400 is moved horizontally towards the centering plate 600 to its second position, the shuttle plate 400 slides adjacent to the centering plates 602a-h such that the separated filters 12 seated in the slots 402a-h get trapped between the slot arms 404a-p and the corresponding notch arms 606a, 606b.

If filters were not intended for a particular assay, the centering plate assembly 600 may be retracted to avoid interference with the coupling of the upper fluid coupling 502a-h to the lower fluid coupling 504a-h. The centering plates 602a-h may be attached to a centering plate bar 612. In the preferred embodiment, the centering plate bar 612 accommodates 6 to 8 centering plates 602a-h. The centering plate bar 612 is mounted on two linear actuators 614, 616 that allow the centering plate bar 612 to move from a fully extended position to a fully retracted position. The fully extended position is used when attaching a filter to the fluid coupling as shown in FIG. 8. The fully retracted position is used when no filter is desired. A sensor 622, 624 may be provided on a support wall 613 to detect when the centering plate bar 612 is in its fully retracted position, abutting the support wall 613. In the example shown in FIG. 8, the sensors 622, 624 are mechanical switches that can be closed when the centering plate bar 612 is in a retracted position. Compressing the switches closes a circuit to notify the computer 1000 that the centering plate bar 612 is in the retracted position. In some embodiments, the sensor 622, 624 may detect when the centering plate bar 612 is in its fully extended position. The actuator for the centering plate movement may use a motor 618, 620, such as a stepper motor variety with 0.5 inch stroke.

In some embodiments, a switch may be operatively connected to the shuttle plate 400 and/or the centering plate 600 so as to detect when the filter is in the proper position to connect with the fluid coupler 500. For example, the switch can be a pressure sensitive switch, an optical switch, and the like. In some embodiments, a switch may be actuated when the shuttle plate 400 traps the separated filter 12a against the centering plate assembly 600. In some embodiments, an optical switch may be used to detect when a filter has been misaligned along the vertical axis. In some embodiments, the process may be dependent on timing, since it can be determined how long each step takes.

For ease of description, the following description of one slot, one notch and one filter is applicable to all of the slots and their corresponding notches and filters. With reference to FIG. 9D, the centering plate 602a is positioned so that when the shuttle plate 400 presses the separated filter 12a against the notch arms 606, 608, the inlet 14 and outlet 16 of the separated filter 12a is aligned with the vertical axis B of the fluid couplings 502a, 504a to allow the lower fluid coupling 504a and the upper fluid coupling 502a to attach to the separated filter 12a to complete a fluidic path as shown in FIG. 9E. For example, the centering plates 602a may be slightly below the shuttle plate 400. Thus, as the shuttle plate 400 approaches the centering plate 602a, the outlet 16 (or inlet 14) of the filter 12a abuts against the notch arms 606, 608 of the centering plates 602a. Due to the "V" or "U"-shaped configuration, the outlet 16 (or inlet 14) of the filter 12a is pushed into the center of the notch 604a as the slot arms 404a, 404b of the shuttle plate 400 traps the outlet 16 (or inlet 14) against the notch arms 606a, 606b of the centering plate 602a. Preferably, the filters have a smooth, non-threaded major portion on the outside diameter of the outlet (or inlet) portion of the filter to ensure proper centering. In addition, the centering plate 602a may be spring-loaded 610 to push and center the separated filter to a known and repeatable position that is adequate for connecting to the fluid coupling.

Upon completion of the filtering process, the upper and lower fluid couplings 502a-h, 504a-h move away from each other back into their original positions to decouple from the separated filter 12a or from each other as shown in FIG. 9F. The shuttle plate 400 can move in a second horizontal direction opposite the first horizontal direction, back to the first position to catch more separated filters and repeat the process.

As shown in FIG. 9G, during this process, the shuttle plate 400 may overshoot the first position to a third position for discarding the separated filter 12a from the shuttle plate 400. Adjacent to the shuttle plate 400 may be a discard bar 422. There is a clearance between the shuttle plate 400 and the discard bar 422 so that the shuttle plate 400 can slide under or over the discard bar 422; however, the clearance is small enough so that any separated filter 12a seated on the shuttle plate 400 will abut against the discard bar 422. The discard bar 422 remains fixed while the shuttle plate 400 continues to slide causing the separated filter 12a to move along the slot arms 404a, 404b. Once the separated filter 12a reaches the opening 402a-h of the slot arm 404a, 404b, the separated filter 12a slides off the shuttle plate 400 and falls into a bin 116 for recovery. Alternatively, the shuttle plate 400 may remain in the first position and the discard bar 422 may move across the shuttle plate 400 to push the filters 12a off the shuttle plate 400.

Various other means for discarding the separated filter 12 from the shuttle plate 400 can also be used. For example, the shuttle plate 400 may be able to tilt downwardly so that the separated filters 12 can slide of the slot arms by the force of gravity. In another embodiment, an ejector may be positioned below shuttle plate 400 to pop the separated filter 12 out of the slot 402a-h vertically. In another embodiment, the slot arms 404a-p may be moveable in a lateral direction so that the slot arms 404a-p move away from each other increasing the width of the slot 402a-h until it becomes larger than the diameter of the filter body 18 causing the filter body 18 to fall through the enlarged slot.

In certain times, it may be desired to collect a sample without the need for filtering the sample prior to collection. The shuttle plate 400 may be placed in the third position offset from the filter stacks 10 and away from the center plate assembly 600 to allow the released filter to drop below the shuttle plate 400. Alternatively, the rollers 402, 404 may temporarily stop so that no filters are discharged. In some embodiments, the separated filters 12 may drop into the shuttle plate 400, but the shuttle plate 400 may be temporarily disabled so as not to move the filter to the fluid coupler 500. In some embodiments, it may be desirous to have some fluidic paths to contain filters while others do not. Therefore, in some embodiments, each slot may be independent of the other and may move filters into and out of the fluid coupler 500 accordingly.

In some embodiments, the filters 12 may be reused. For example, it may be desirable to collect a sample of fluid with filtration, then collect another sample of the same fluid without filtration, and then collect the third sample of the same fluid with filtration again. In this instance, since the same fluid is being sampled, the filters 12 may be reused. For such a use, the filters 12 can be coupled to the fluid couplings 502a-h, 504a-h as discussed above. Upon completion of obtaining a filtered sample, the fluid couplings 502a-h, 504a-h can be disconnected from the filters 12 and the filters 12 can be moved away from the fluid couplings 502a-h, 504a-h to allow the fluid couplings 502a-h, 504a-h to connect to itself. Upon completion of obtaining a non-filtered sample, the fluid couplings 502a-h, 504a-h can disconnect themselves and the filters 12 can move back into position so that the fluid couplings 502a-h, 504a-h can connect with the filters 12 again. In some embodiments, when the system is collecting a non-filtered sample, the shuttle plate 400 may move the filters 12 to the first position or the third position so as to hold the filters 12 without discarding them for the purpose of using them at a later time. When ready to reuse, the shuttle plate 400 will move the filter 12 back into position in between the fluid couplings 502, 504.

To assure proper functioning and full automation, one or more sensors may be utilized to detect a proper positioning of the filters 12, the shuttle plate 400, the centering plate 600, the fluid couplings 500, and the like. Fail safe mechanisms may be put into place to stop the system in the event one or more component is not in its proper position. Sensors may be provided to verify all intended filters have been loaded on the shuttle plate, and preferably, in the fluid coupling position. If, for example, a sensor detects that a filter is missing, or a filter is in the wrong orientation, then the shuttle plate 400 will be programmed to discard the filters 12. The shuttle plate 400 will then return to its first position for loading of new filters. In the preferred embodiment, the cycle may happen up to two times before the unit stops and an error message is displayed.

All components requiring movement may utilize a motor. In the preferred embodiment, all motion, except for the centering plate, may be driven by a 200 step/rev., 12 V stepper motor. The motors may have programmable speed and acceleration profiles. The motor current may be programmable for various torque requirements. The motors for the shuttle plate and the fluid coupling may have encoders mounted to them.

To minimize or avoid corrosion, all components in the device, such as tubing, fluid couplers, and the like, may be made of corrosion resistant material such as plastic, rubber, and the like. In addition, a fan may be attached to the housing to keep the components cool; however, to reduce the fumes inside the housing, the fan is configured to exhaust the air out of the housing. Furthermore, any lead screws used to move the various components may have a protective coating.

In use, the automatic filter changer 100 can be programmed to operate with a filter 12 in place, operate without a filter 12 in place, and change the filter 12 based on a predetermined condition. The automatic filter changer 100 may be set up in two different configurations, a pull through configuration or a push through configuration. In the pull through configuration, the filters 12 are upstream of the pump and the pump action pulls the fluid through the filters. In the push through configuration the filters 12 are downstream of the pump and the pump action pushes the fluid through the filters.

The user creates a stack of filters 10 by inserting one end of the first filter into the second end of a second filter. For example, the user may insert the outlet 16 of one filter 12a into the inlet 14 of the second filter 12a'. This process continues until the user has a desired number of filters in one stack. For example, one filter stack 10 may contain 25 individual filters. Once a stack of filters 10 is created, the user can insert the filter stack 10 into a filter tube 216 of a filter stack block 200. Generally, the filter stack block 200 has 6 to 8 holes to receive 6 to 8 filter stacks. In some embodiments, a filter manufacturer may sell pre-stacked filters. Therefore, a user may simply open a package of pre-stacked filters 10 and insert them into the filter tubes 216a-h. The filter stacks 10a-h will fall through the filter tubes 216a-h and through the holes 214a-h of the filter stack block 200 until the lead filter 12 lands on the filter separator 300 to begin the process described herein.

Due to the modular and self-contained nature of the automatic filter changer 100, the automatic filter changer 100 can be used with other existing devices, such as existing dissolution systems. The user needs only to hook up the fluid coupler with the tubing of the dissolution system and a collection device or measuring device.

Once the connections and filters are in place, the user can access the graphic user interface generally located on the front side of the automatic filter changer 100. From there, the user can program the automatic filter changer 100 to run according to specified instructions. These instructions can be saved for later use. In some embodiments, a predetermined set of instructions may be stored in memory of the automatic filter changer 100. The user will be able to access any predetermined set of instructions and run any of those sets of instructions accordingly.

If the program has been set to utilize filters 12, the rollers 302, 304 will begin rotating about their respective longitudinal axes L1, L2 in opposite directions. When one of the matching indentation pairs reaches the top side 310 of the rollers 302, 304, the filter body 18 of the lead filter 12a will drop into the matching indentation pair 316a, 318a. As the rollers 302, 304 continue to rotate, the matching indentation pair 316a, 318a will enter into the gap 306 creating an enlarged gap defined by the indentations 316a, 318a of the two rollers 302, 304. Since the filter 12a resides within the indentations 316a, 318a, the filter 12a is able to pass in between the rollers 302, 304. In the meanwhile, the remainder of the filter stack 10a continues to sit on top of the two rollers 302, 304 because the filter body 18 is too wide to the pass through the gap 306 defined by the two rollers 302, 304 when the matching indentation pair 316a, 318a is not available. Furthermore, due to the angular offset of the other matching indentation pairs, the lead filters 12 of each of the other filter stacks 10a-h remain on top of the roller pairs 302, 304 until the first lead filter 12 has been completely separated from its respective filter stack 10.

As the matching indentation pairs 316a, 318a for the lead filter 12 reaches the bottom side 312 of the rollers 302, 304, the first lead filter 12 is separated from the stack 10 and dropped onto the shuttle plate 400 located directly below the rollers 302, 304. In this example, the outlet 16 or inlet 14 falls through the slot 402 of the shuttle plate 400 and the body 18 rests on the top surface of the shuttle plate 400. In the meanwhile, the other lead filters 12 are being separated from their filter stacks 10b-h in sequential order. Therefore, each lead filter 12 will eventually fall onto the shuttle plate 400, but one at a time.

The shuttle plate 400 may pause for a few seconds (e.g. less than five seconds) to allow the separated filters 12 to stabilize on the shuttle plate 400. In some embodiments, the shuttle plate 400 may jiggle to force the separated filters 12 to settle into the shuttle plate 400. Sensors will be put into place to assure that a filter has dropped from each filter stack and that the separated filters are properly seated on the shuttle plate 400. If there is an error in the seating of the separated filters, the shuttle plate 400 will move from its first position (the load position) to its third position (the discard position) to force all of the separated filters 12 off the shuttle plate 400. The shuttle plate 400 will then revert back to its first position and new filters will be loaded onto the shuttle plate 400.

By way of example only, to detect whether each filter has been properly seated, the underside of the shuttle plate 400 may have an alignment bar 424. The alignment bar 424 spans substantially the full length of the shuttle plate 400 and is within the same horizontal plane defined by the centering plates 602. Thus, if the shuttle plate 400 moved horizontally to the centering plate assembly 600 without stopping, the centering plate assembly 600 would abut against the alignment bar 424 of the shuttle plate 400.

The dimensions of the slot 402 and the dimensions of the notch 604 are precisely configured so that when the inlet 14 of the filter 12 is trapped in between the slot 402 and the notch 604, a gap exists between the centering plate 602 and the alignment bar 424 due to the thickness of the inlet 14 as shown in FIGS. 9D-9F.

Figure 9H:
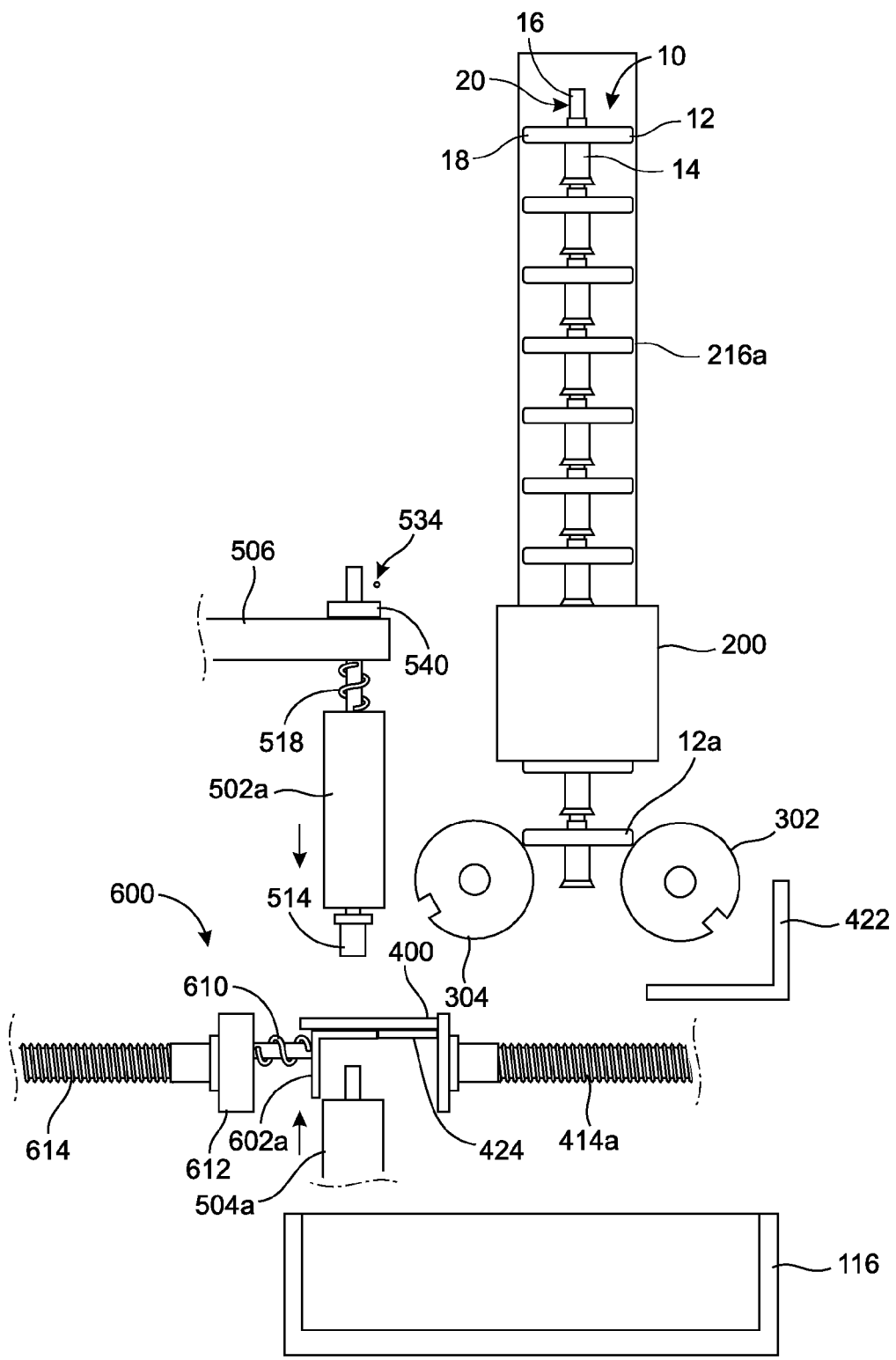

If, on the other hand, a filter 12 is not seated in the slot 402, then since there is nothing obstructing the path between the shuttle plate 400 and the centering plate assembly 600, the alignment bar 424 will press against the notch arms 606, 608 as shown in FIG. 9H. The centering plate 600 and the shuttle plate 400 are both electrically conductive. When the alignment bar 424 presses against the notch arms 606, 608, this closes a circuit and sends a signal to the computer to indicate an improper alignment or a missing filter 12 on the shuttle plate 400.

Figure 9I:
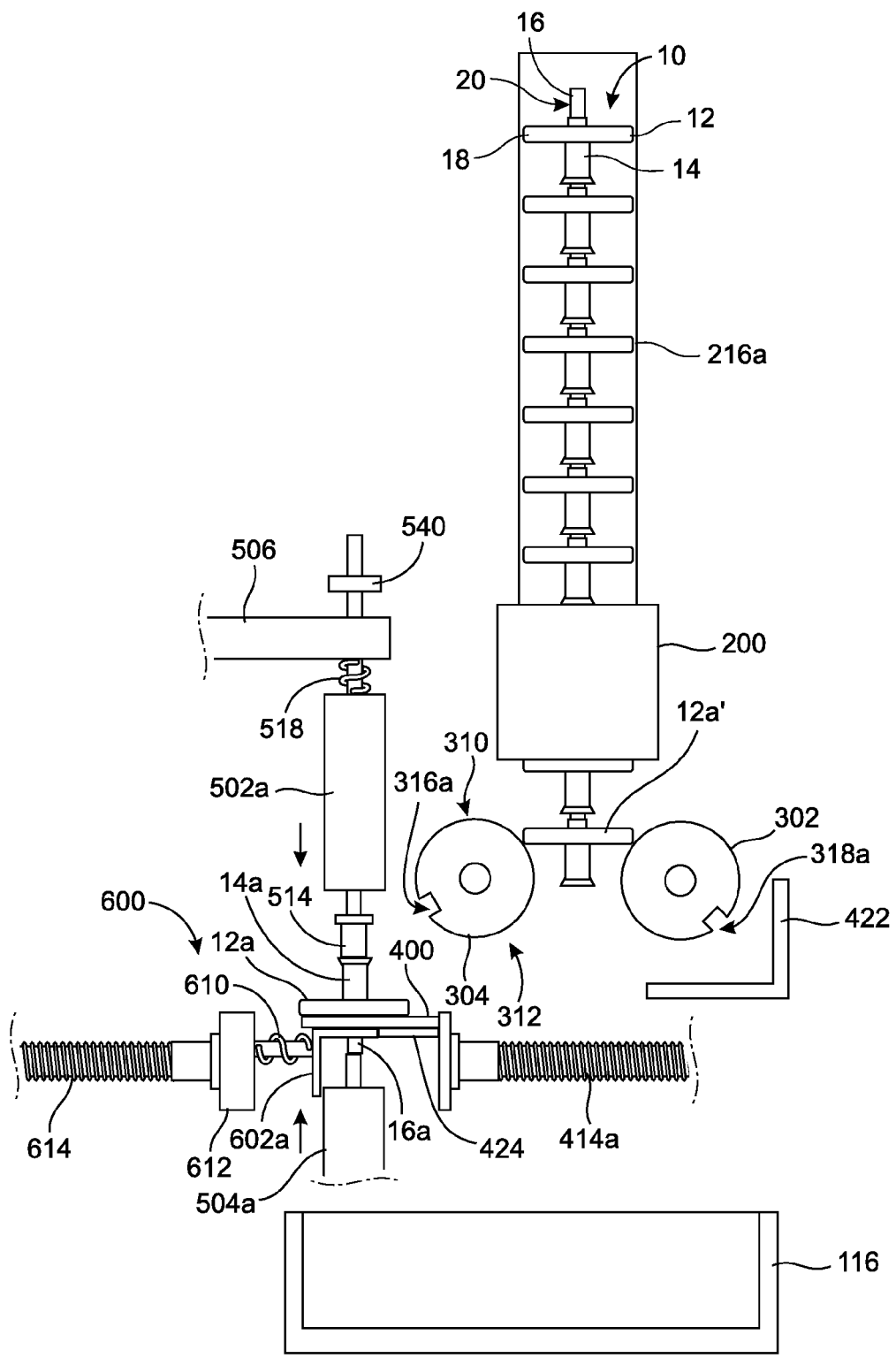
Figure 10:
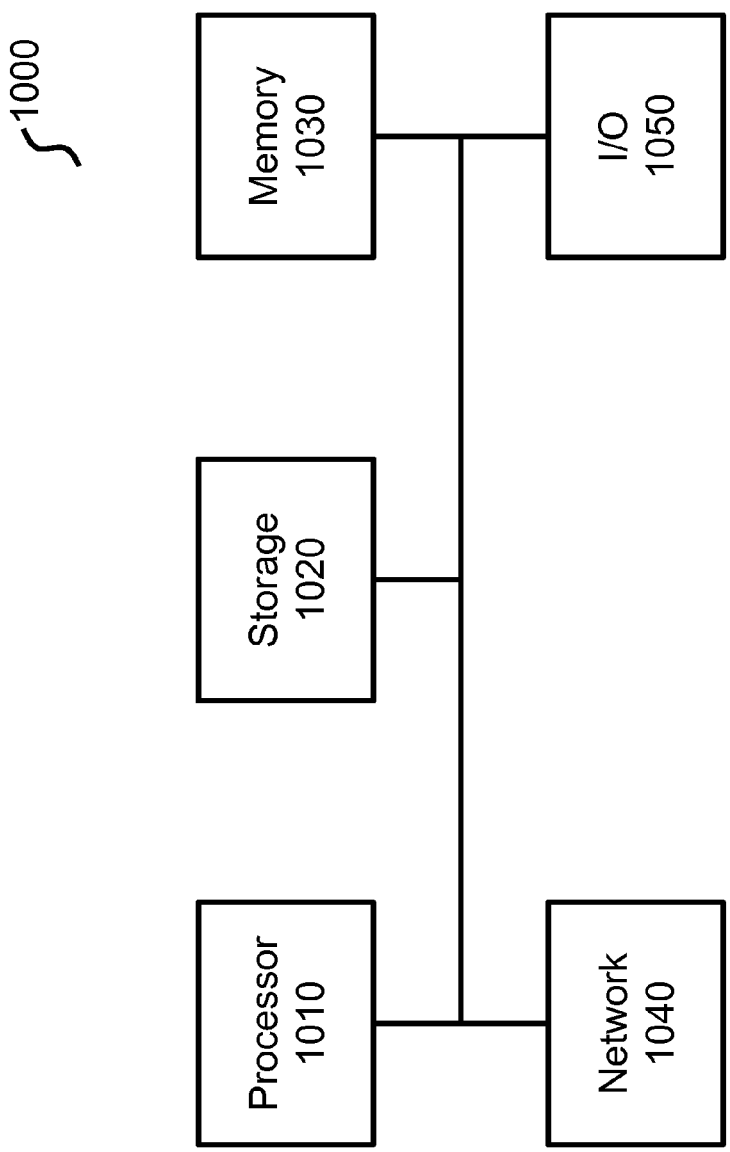
FIG. 10 shows an embodiment of a computer architecture for automatically operating the present invention.

Similarly, as shown in FIG. 9I, if the outlet 16, instead of the inlet 14, has fallen through the slot 402, the notch 604 in the slot 602 are configured such that the notch arms 606, 608 will abut against the alignment bar 424 before the outlet 16 is trapped in between the notch arms 606, 608 and the slot arms 404 because the outlet 16 has a diameter that is smaller than the diameter of the inlet 14. Contact between the alignment bar 424 and the notch arms 606, 608 again closes a circuit, and sends a signal to the computer to indicate that there has been a misalignment of the filter. Similar function can be achieved with optical sensors, switches, and the like.

Once all separated filters 12a-h have been properly seated on the shuttle plate 400, the shuttle plate 400 advances to its second position towards the back of the housing 102 for coupling with the fluid couplers 500. Eventually, the shuttle plate 400 will slide adjacent to the centering plate assembly 600. As the shuttle plate 400 slides adjacent to the centering plate 600, the shuttle plate 400 presses the filter 12 into the notch 604a of the centering plate 602a, thereby trapping the filter 12 in between the shuttle plate 400 and centering plate 602a. Preferably, the portion of the filter 12 projecting below the shuttle plate 400 (i.e. the outlet or the inlet of the filter) is caught between the slot 402a of the shuttle plate 400 and the notch 604a of the centering plate 602a.

The positioning of centering plate 602a is such that when the filter 12 is caught between the shuttle plate 400 and the centering plate 602a as described above, the inlet 14 and outlet 16 of the filter 12 aligns with the fluid coupler 500, which comprises a first fluid coupling 502a and a second fluid coupling 504a. The first and second fluid couplings 502a, 504a then move toward each other until the fluid couplings 502a, 504a are fitted with the inlet 14 and the outlet 16 of the filter 12.

A pump generates a force through the tubes causing the fluid to move from the dissolution apparatus through the filters 12 and to the collection device or the measurement device. When collection of the fluid sample is complete, the filters 12 may be left in place waiting for another sample or the first and second fluid coupling 502a, 504a move away from each other releasing themselves from the filter 12. The shuttle plate 400 then moves towards the third position. In doing so, a discard bar 422 knocks the filters 12 off of the shuttle plate 400. The shuttle plate 400 can then return to its first position to load a new set of clean filters.

In embodiments in which a filter is not necessary, the separator 300 or the shuttle plate 400 can be stopped. The centering plate assembly 600 may retract to create any clearance necessary to allow the first fluid coupling and the second fluid coupling 502a, 504a to move towards each other and couple to each other to complete the fluidic path and allow fluid flow from the dissolution apparatus to the collection or measuring device without having been filtered.

The automated filter changer may further comprise a computer to control and program various protocols for collecting samples with or without filters. The computer is programmable to execute instructions for moving the various components described above to automatically provide and remove filters from a fluidic path. The computer system may comprise a monitor to display a graphic user interface to receive and transmit information.

In various embodiments, the method steps described herein, including the method steps described in the figures, may be performed in an order different from the particular order described or shown. In other embodiments, other steps may be provided, or steps may be eliminated, from the described methods.

The computer 1000 comprises a processor 1010 operatively coupled to a data storage device 1020 and memory 1030. The processor 1010 controls the overall operation of computer by executing computer program instructions that define such operations. The computer program instructions may be stored in data storage device 1020, or other non-transitory computer readable medium, and loaded into memory 1030 when execution of the computer program instructions is desired. Thus, the method steps can be defined by the computer program instructions stored in memory 1030 and/or data storage device 1020 and controlled by processor 1010 executing the computer program instructions.

For example, the computer program instructions can be implemented as computer executable code programmed by one skilled in the art to perform an algorithm defined by the method steps. The computer 1000 may also include one or more network interfaces 1040 for communicating with other devices via a network. The computer 1000 may also include one or more input/output devices 1050 that enable user interaction with computer (e.g., display, keyboard, touchpad, mouse, speakers, buttons, etc.).

The processor 1010 can include, among others, special purpose processors with software instructions incorporated in the processor design and general purpose processors with instructions in storage device or memory, to control the processor, and may be the sole processor or one of multiple processors of computer. The processor 1010 may be a self-contained computing system, containing multiple cores or processors, a bus, memory controller, cache, etc. A multi-core processor may be symmetric or asymmetric. The processor 1010, data storage device 1020, and/or memory 1030 may include, be supplemented by, or incorporated in, one or more application-specific integrated circuits (ASICs) and/or one or more field programmable gate arrays (FPGAs). It can be appreciated that the disclosure may operate on a computer with one or more processors or on a group or cluster of computers networked together to provide greater processing capability.

Data storage device 1020 and memory 1030 each comprise a tangible non-transitory computer readable storage medium. By way of example, and not limitation, such non-transitory computer-readable storage medium can include random access memory (RAM), high-speed random access memory (DRAM), static random access memory (SRAM), double data rate synchronous dynamic random access memory (DDRRAM), read-only memory (ROM), erasable programmable read-only memory (EPROM), electrically erasable programmable read-only memory (EEPROM), flash memory, compact disc read-only memory (CD-ROM), digital versatile disc read-only memory (DVD-ROM) disks, or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

In some embodiments, a network/communication interface 1040 enables the computer 1000 to communicate with networks, such as the Internet, also referred to as the World Wide Web (WWW), an intranet and/or a wireless network, such as a cellular telephone network, a wireless local area network (LAN) and/or a metropolitan area network (MAN), and other devices using any suitable communications standards, protocols, and technologies. By way of example, and not limitation, such suitable communications standards, protocols, and technologies can include Ethernet, Wi-Fi (e.g., IEEE 802.11), Wi-MAX (e.g., 802.16), Bluetooth, near field communications ("NFC"), radio frequency systems, infrared, GSM, EDGE, HS-DPA, CDMA, TDMA, quadband, VoIP, IMAP, POP, XMPP, SIMPLE, IMPS, SMS, or any other suitable communications protocols. By way of example, and not limitation, the network interface 1040 enables the computer 1000 to transfer data, synchronize information, update software, or any other suitable operation.

Input/output devices 1050 may include peripherals, such as a printer, scanner, monitor, etc. Input/output devices 1050 may also include parts of a computing device, such as a smartphone having a touchscreen, speakers, and buttons. For example, input/output devices 1050 may include a display device such as a liquid crystal display (LCD) monitor for displaying information to the user, a keyboard and mouse by which the user can provide input to the computer, or a touchscreen for both input and output.

Any or all of the systems and apparatus discussed herein, including personal computers, tablet computers, hand-held devices, cellular telephones, servers, database, cloud-computing environments, and components thereof, may be implemented using a computer.

One skilled in the art will recognize that an implementation of an actual computer or computer system may have other structures and may contain other components as well.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:
1. An automatic filter changer, comprising:
  a. housing;
  b. a filter stack block attached to the housing, the filter stack block comprising a plurality of holes to receive a plurality of filter stacks, wherein each hole is configured to receive one filter stack, wherein each filter stack comprises a plurality of filters, each filter having an inlet, a filter body attached to the inlet, and an outlet attached to the filter body opposite the inlet;
  c. a plurality of filter stack tubes to support and help feed the plurality of filter stacks into the filter stack block, each hole of the filter stack block configured to receive one filter stack tube;
  d. a filter separator positioned below the filter stack block to separate from each filter stack a first filter from its respective filter stack, sequentially so that the first filter from a first stack is separated before the first filter of a second stack, the filter separator comprising a pair of rollers to release the filters from their respective filter stacks, each roller comprising an elongated bar having a longitudinal axis, a first cylinder, a last cylinder, and a plurality of intermediate cylinders in between the first cylinder and the last cylinder, each cylinder attached to the elongated bar in series along the longitudinal axis, wherein each cylinder has a first end and a second end, wherein each intermediate cylinder comprises two indentations, a first indentation formed at the first end and a second indentation formed at the second of each intermediate cylinder, wherein the first indentation and the second indentation within any intermediate cylinder is angularly offset from each other about the longitudinal axis, and wherein the second indentation of one intermediate cylinder is in line with the first indentation of an immediately adjacent cylinder to form an indentation pair between two immediately adjacent cylinders, wherein the pair of rollers are arranged parallel to each other defining a gap, wherein the pair of rollers a configured to rotate in opposite direction about their respective longitudinal axes such that opposing indentation pairs face each other in the gap in series, wherein each indentation pair is configured to receive and separate one filter from one of the filter stacks sequentially;
  e. a shuttle plate positioned below the filter separator to catch a released filter, the shuttle plate comprising a plurality of slots defined by slot arms, each slot aligning with one filter stack, wherein the shuttle plate is movable in a horizontal direction to carry a set of released filters to a series of fluid couplers, wherein each fluid coupler comprises an upper fluid coupling and a lower fluid coupling coaxially aligned with the upper fluid coupling, the upper fluid coupling and the lower fluid coupling defining a vertical axis;
  f. a plurality of centering plates, one centering plate aligned with each fluid coupler such that each centering plate is in between one upper fluid coupling and its respective lower fluid coupling, each centering plate comprising a notch defined by notch arms, wherein each notch is aligned with one slot of the shuttle plate such that when the shuttle plate having released filters seated within each slot is moved horizontally towards the centering plates, the shuttle plate slides adjacent to the centering plates causing the slot arms and the notch arms to trap the released filter within the notch and slot, whereby the inlet and outlet of each filter is aligned with the vertical axis defined by their respective upper fluid coupling and the lower fluid coupling to allow the lower fluid coupling and the upper fluid coupling to attach to the released filter to complete a fluidic path;
  g. a plurality of sensors to detect a proper positioning of the filters; and
  h. a computer programmable to execute a change in the filters according to a predetermined set of instructions, wherein the computer comprises a monitor to display a graphic user interface to receive and transmit information.

2. An automatic filter changer, comprising:
a. housing;
b. a filter stack block attached to the housing, the filter stack block comprising a plurality of holes to receive a plurality of filter stacks, wherein each hole is configured to receive one filter stack;
c. a filter separator positioned below the filter stack block, the filter separator configured to separate one filter at a time from each filter stack away from its respective filter stack sequentially so that a first filter from a first filter stack is separated before a first filter of a second filter stack;
d. a shuttle plate positioned below the filter separator to a released filter, wherein the shuttle plate is movable in a horizontal direction to carry a set of released filters to a fluid coupler, wherein the fluid coupler comprises upper fluid couplings and lower fluid couplings, one upper fluid coupling being coaxially aligned with one lower fluid coupling, the upper fluid coupling and the lower fluid coupling defining a vertical axis;
e. a plurality of centering plates, one centering plate aligned with each fluid coupler such that each centering plate is in between one upper fluid coupling and its respective lower fluid coupling, each centering plate comprising a notch defined by notch arms, wherein the filter separator comprises a pair of rollers each defining a longitudinal axis, wherein the pair of rollers is arranged parallel to each other and separated from each other by a gap, wherein each roller comprises a plurality of indentations, wherein each indentation on a first roller corresponds with an indentation on a second roller to form a plurality of matching indentation pairs such that the corresponding indentations of each matching indentation pairs face each other in the gap during rotation, wherein each indentation on the first roller are angularly offset about the longitudinal axis of the first roller from every other indentation on the first roller, and each indentation on the second roller are angularly offset about the longitudinal axis of the second roller from every other indentation on the second roller.

3. The filter changer of claim 2, wherein the pair of rollers is configured to rotate in opposite direction about their respective longitudinal axes such that matching indentation pairs face each other in the gap in series, wherein each indentation pair is configured to release one filter from one of the filter stacks in series.

4. The filter changer of claim 2, wherein the fluid coupler comprises an optical emitter to emit a beam of light, and an optical detector to receive the beam of light, wherein the beam of light is obstructed by one of the fluid couplings when the filter is improperly seated.

5. The filter changer of claim 2, further comprising a computer programmable to execute a change in the filters according to a predetermined set of instructions, wherein the computer comprises a monitor to display a graphic user interface to receive and transmit information.

6. An automatic filter changer, comprising:
a. housing;
b. a filter stack block attached to the housing, the filter stack block comprising a plurality of holes to receive a plurality of filter stacks, wherein each hole is configured to receive one filter stack;
c. a filter separator positioned below the filter stack block, the filter separator configured to separate one filter at a time from each filter stack away from its respective filter stack sequentially so that a first filter from a first filter stack is separated before a first filter of a second filter stack;
d. a shuttle plate positioned below the filter separator to catch a released filter, wherein the shuttle plate is movable in a horizontal direction to carry a set of released filters to a fluid coupler, wherein the fluid coupler comprises upper fluid couplings and lower fluid couplings, one upper fluid coupling being coaxially aligned with one lower fluid coupling, the upper fluid coupling and the lower fluid coupling defining a vertical axis;
e. a plurality of centering plates, one centering plate aligned with each fluid coupler such that each centering plate is in between one upper fluid coupling and its respective lower fluid coupling, each centering plate comprising a notch defined by notch arms, wherein the shuttle plate comprises a plurality of slots defined by slot arm pairs, each slot configured to align with one filter stack when the shuttle plate is in a first position, and each slot configured to align with one of the vertical axes defined by one pair of upper fluid couplings and lower fluid couplings when the shuttle plate is in a second position.

7. The filter changer of claim 6, wherein each notch of the centering plate is aligned with one slot of the shuttle plate such that when the shuttle plate is moved horizontally towards the centering plates, the shuttle plate slides adjacent to the centering plate such that when at least one released filter is seated in at least one slot, the slot arms and the notch arms trap the at least one released filter within its respective notch and slot, wherein the inlet and outlet of the at least one released filter is aligned with the vertical axis of its respective upper and lower fluid coupling to allow the lower fluid coupling and the upper fluid coupling to attach to the at least one released filter to complete a fluidic path.

8. The filter changer of claim 6, wherein the shuttle plate is positionable in a third position offset from the filter stacks and away from the center plates to allow the released filter to drop below the shuttle plate.

9. The filter changer of claim 6, wherein slot arms within a slot arm pair converge toward each other at an opening of the slot.

10. The filter changer of claim 6, wherein the shuttle plate further comprises an alignment bar configured to abut against one of the centering plates when the filter is not properly seated on the shuttle plate.

11. The filter changer of claim 6, wherein the fluid coupler comprises an optical emitter to emit a beam of light, and an optical detector to receive the beam of light, wherein the beam of light is obstructed by one of the fluid couplings when the filter is improperly seated.

12. The filter changer of claim 6, further comprising a computer programmable to execute a change in the filters according to a predetermined set of instructions, wherein the computer comprises a monitor to display a graphic user interface to receive and transmit information.

13. The filter changer of claim 6, wherein the filter separator comprises a pair of rollers each defining a longitudinal axis, wherein the pair of rollers is arranged parallel to each other and separated from each other by a gap, wherein each roller comprises a plurality of indentations, wherein each indentation on a first roller corresponds with an indentation on a second roller to form a plurality of matching indentation pairs such that the corresponding indentations of each matching indentation pairs face each other in the gap during rotation.

\* \* \* \* \*